US009896473B2

(12) United States Patent
Morvan et al.

(10) Patent No.: US 9,896,473 B2
(45) Date of Patent: Feb. 20, 2018

(54) THIOL COMPOUNDS AND THE USE THEREOF FOR THE SYNTHESIS OF MODIFIED OLIGONUCLEOTIDES

(71) Applicants: CENTRE NATIONAL DE LA RECHERCHE SCIENTIFIQUE (CNRS), Paris (FR); UNIVERSITE DE MONTPELLIER 1, Montpellier (FR); ETABLISSEMENT FRANÇAIS DU SANG, La Plaine St-Denis (FR); UNIVERSITE CLAUSE BERNARD LYON 1, Villeurbanne (FR)

(72) Inventors: François Morvan, Castelnau le Lez (FR); Albert Meyer, Perols (FR); Jean-Jacques Vasseur, Combaillaux (FR); Julie Mayen, Vedene (FR); Carole Chaix, Chaponnay (FR); Carole Farre, Lyons (FR); Chantal Fournier-Wirth, La Plaine Saint Denis (FR); Jean-François Cantaloube, La Plaine Saint Denis (FR); Myriam Lereau, La Plaine Saint Denis (FR)

(73) Assignees: Etablissement Francais du Sang, Saint Denis (FR); Centre National de la Recherche Scientifique (CNRS), Paris (FR)

( * ) Notice: Subject to any disclaimer, the term of this patent is extended or adjusted under 35 U.S.C. 154(b) by 451 days.

(21) Appl. No.: 14/390,747

(22) PCT Filed: Apr. 4, 2013

(86) PCT No.: PCT/EP2013/057122
§ 371 (c)(1),
(2) Date: Oct. 3, 2014

(87) PCT Pub. No.: WO2013/150106
PCT Pub. Date: Oct. 10, 2013

(65) Prior Publication Data
US 2015/0158964 A1 Jun. 11, 2015

(30) Foreign Application Priority Data
Apr. 4, 2012 (FR) ...................... 12 53121

(51) Int. Cl.
*C07H 21/04* (2006.01)
*C07F 9/24* (2006.01)
(Continued)

(52) U.S. Cl.
CPC .......... *C07H 21/04* (2013.01); *C07C 323/52* (2013.01); *C07F 9/2408* (2013.01); *C08F 257/02* (2013.01); *C12N 15/11* (2013.01)

(58) Field of Classification Search
CPC ..................................................... C07H 21/04
(Continued)

(56) References Cited

PUBLICATIONS

International Search Report dated May 31, 2013, PCT Application No. PCT/EP2013/057122, filed Apr. 4, 2013, 2 pages.
(Continued)

*Primary Examiner* — Jezia Riley
(74) *Attorney, Agent, or Firm* — Marsh Fischmann & Breyfogle LLP

(57) ABSTRACT

The present invention relates to a thiol compound suitable for forming a chain of oligomers that can be grafted to an oligonucleotide. The invention also relates to an oligonucleotide grafted by such a compound, thus having one or more thiol functions, suitable for being immobilized on a gold surface or on a grafted surface.

7 Claims, 16 Drawing Sheets

(51) Int. Cl.
*C07C 323/52* (2006.01)
*C08F 257/02* (2006.01)
*C12N 15/11* (2006.01)

(58) Field of Classification Search
USPC .......................................................... 536/23.1
See application file for complete search history.

(56) References Cited

PUBLICATIONS

Shigdel et al., "A New 1'—Methylenedisulfide Deoxyribose that Forms an Efficient Cross-Link to DNA Cytosine-5 Methyltransferase (DNMT)", Journal of the American Chemical Society, vol. 130, No. 52, Dec. 31, 2008, pp. 17634-17635.

Jin et al., "Synthesis of Amine-and Thiol-Modified Nucleoside Phosphoramidites for Site-Specific Introduction of Biophysical Probes into RNA", The Journal of Organic Chemistry, vol. 70, No. 11, May 1, 2005, pp. 4284-4299.

Hatano et al., "Synthesis and redox-active base-pairing properties of DNA incorporating mercapto C-nucleosides", Tetrahedron, Elsevier Science Publishers, Amsterdam, NL, vol. 61, No. 7, Feb. 14, 2005, pp. 1723-1730.

Z Kupihar, "Synthesis and application of a novel, crystalline phosphoramidite monomer with Thiol Terminus, suitable for the synthesis of DNA conjugates", Bioorganic & Medical Chemistry, vol. 9, No. 5, May 1, 2001, pp. 1241-1247.

Figure 13b
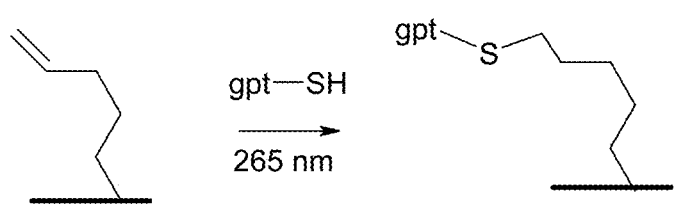
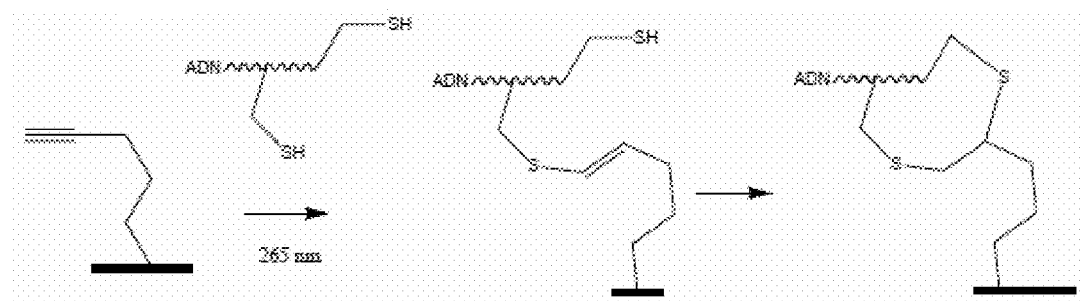

SEQUENCE LISTING

<160> NUMBER OF SEQ ID NOS: 3

<210> SEQ ID NO 1
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="biotinylated HCV sense primer"
      /organism="artificial sequences"

<400> SEQUENCE: 1
tggggatccc gtatgatacc cgctgctttg a                              31

<210> SEQ ID NO 2
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="HCV antisense primer"
      /organism="artificial sequences"

<400> SEQUENCE: 2
ggcggaattc ctggtcatag cctccgtgaa                                30

<210> SEQ ID NO 3
<211> LENGTH: 13
<212> TYPE: DNA
<213> ORGANISM: artificial sequences
<220> FEATURE:
<221> NAME/KEY: source
<222> LOCATION: 1..13
<223> OTHER INFORMATION: /mol_type="DNA"
      /note="nucleic acid graft test"
      /organism="artificial sequences"

<400> SEQUENCE: 3
ccaagcacga tgt                                                  13

THIOL COMPOUNDS AND THE USE THEREOF FOR THE SYNTHESIS OF MODIFIED OLIGONUCLEOTIDES

TECHNICAL FIELD

The present invention relates to a thiol compound suitable for forming a chain of oligomers that can be grafted to an oligonucleotide. The invention also relates to an oligonucleotide grafted by such a compound, thus having one or more thiol functions, suitable for being immobilized on a gold surface or on a grafted surface, in particular a surface grafted by maleimide or acrylamide functions. The invention also relates to a kit of detection test of interaction between nucleotides and other molecules using as surface, the gold surface or the grafted surface, notably by maleimide or acrylamide functions on which the oligonucleotides according to the invention are immobilized.

STATE OF THE ART

Oligonucleotides are molecules comprising a short chain nucleotide, the number of nucleotides ranging from 1 to about 100. They are fragments of RNA (ribonucleic acid) or DNA (deoxyribonucleic acid). Oligonucleotides are generally synthesized as single strands.

The oligonucleotides can be synthesized by enzymatic means or by chemical synthesis methods. When selecting a chemical method, typically, the oligonucleotides are synthesized on a solid support by techniques well known to those skilled in the art, for example by implementing a method using phosphoramidites, H-phosphonates, or phosphodiester phosphotriesters, the latter two compounds are derivatives of phosphoric acid, while the phosphoramidites are derivatives of phosphorous acid.

An important property of the oligonucleotides is their ability to control the gene and protein function in a specific sequence. This property renders the oligonucleotides and their derivatives compounds widely used in molecular biology research and in many pharmaceutical and diagnostic applications. The research needs to have available large quantities of oligonucleotides. Thus, a method for producing large quantities of oligonucleotides of very high purity is required.

Nucleic acids having a particular nucleotide sequence are widely used for the detection of DNA in biological samples. The principle of this detection test relies on the complementarity of the nucleotide sequence with the target sequence, thereby forming a double strand. This double strand is formed during a process called hybridization.

This hybridization phenomenon can then be detected by various methods, in particular the marking of the nucleotide sequence intended for binding to the sequence initially present. Fluorescent or radioactive marking methods, for detecting hybridization phenomenon have certain disadvantages. Marking requires an additional step during the synthesis of the nucleotide sequence, this step is sometimes difficult to implement. The test, based on this hybridization phenomenon detected by marking, requires, after the hybridization step, removing marked nucleotide sequences not being bound to the target sequence of the sample.

Other methods of detection were then implemented, in particular methods wherein the nucleotide sequences are first immobilized on a surface, the test sample is then contacted with that surface to create the phenomenon of hybridization by the formation of double strands.

Among these other methods, electrochemical methods are increasingly used. These methods are based on the immobilization of oligonucleotides on an electrode, e.g. a gold electrode. During the test, the hybridization of single-stranded oligonucleotides immobilized on the gold electrode is quantified by measuring the electrical current, which depends on the number of duplexes formed between the immobilized single-stranded oligonucleotide and the oligonucleotide of the sample.

In order to realize those tests, the oligonucleotide is immobilized on the metallic surface, and in particular on a gold surface. This immobilization can notably be obtained by means of a bond between a gold atom and a sulphur atom. However, the Au—S bond is of moderate strength. Thus, a single gold-sulphur bond is not sufficient to immobilize an oligonucleotide on the surface of gold in a very stable manner. In fact, the test methods imply steps, in particular of washing, which generate strong mechanical stresses that may destabilize the Au—S bond.

Document EP 0 523 978 discloses phosphoramidite or phosphonate compounds that can be used for producing thiol-modified oligonucleotides. They can only be introduced once, and only on the 5' end of an oligonucleotide.

Document U.S. Pat. No. 7,601,848 discloses a polyfunctional compound comprising two sulphur atoms that is intended to be incorporated in oligomers in order to create at least two gold-sulphur bonds and thus stabilize the oligonucleotide on the gold surface. Some of these compounds comprise a phosphoramidite function. The compounds used in this document are manufactured from very expensive compounds and coupling of the polyfunctional compound on the oligonucleotides does not have a satisfactory yield owing to the steric hindrance of this compound. In this document, a binding agent is necessary in order to bind the thiol compounds to one another and thus effect multiple introduction of thiol compounds into an oligonucleotide.

U. K. Shigdel and C. He, J. Am. Chem. Soc. 2008, 130(52), 17634-5, describe an oligonucleotide modified by a phosphoramidite function intended to be introduced into an oligonucleotide by this function phosphoramidite. The synthesis of the compound described is carried out in 12 steps.

S. Jin et al., J. Org. Chem. 2005, 70, 4284-4299, describe a nucleoside modified by a phosphoramidite function and a thiol function. The modified nucleosides are used to introduce biophysical probes into RNA. The modified nucleoside is synthesized in 9 steps with an overall yield of 12.5%.

A. Hatano et al. Tetrahedron, 61, 2005, 1723-1730, describe the synthesis of DNA, involving a nucleoside base comprising a phosphoramidite function and a thiophenol function. The modified nucleoside is synthesized in 7 steps with poor yield, less than 5%.

Within the three scientific publications above, the phosphoramidite compound is a modified nucleoside intended to be incorporated into an oligonucleotide via this phosphoramidite function. The starting reagents are expensive, the syntheses are lengthy and complex and the yield of synthesis of these phosphoramidite compounds are low. In addition, the steric hindrance of these osidic compounds is not suitable to a satisfactory grafting onto a surface.

A. A. Rowe et al., Anal. Chem. 2011, 83, 9462-9466 describe a nucleoside compound which can be immobilized on a gold surface for DNA detection. The nucleoside compound is included only once, for immobilization on a gold surface via a single thiol function. The starting reagent is expensive, and the thiol compound is complex to manufacture.

The object of the present invention is to provide a thiol compound at least partially overcoming the aforementioned drawbacks, that is to say, a thiol compound, easy to manufacture, which can be oligomerized in a simple and economic manner, and which is intended to be incorporated into an oligonucleotide and immobilized on a surface.

More particularly, the invention aims at providing a method of easily and efficiently introducing one or more thiol functions into an oligonucleotide.

SUMMARY OF THE INVENTION

The invention firstly relates to a compound corresponding to the following formula (I):

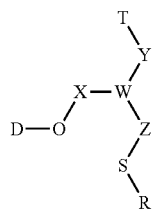

(I)

in which:

T is a group selected from —O—P(OR$_1$)N(R$_2$)$_2$, —O—PH(O)O$^-$, —OC(O)JC(O)NH-☐, R$_1$ is selected from the 2-cyanoethyl, R'$_1$R'$_2$R'$_3$SiCH$_2$CH$_2$, groups and R'$_1$, R'$_2$, R'$_3$, which may be identical or different, represent a group selected from the linear or branched alkyls comprising from 1 to 12 carbon atoms and the C6-C12 aryls, R$_2$ is selected from the linear or branched alkyl groups comprising from 1 to 12 carbon atoms, pyrrolidine, J is selected from a single bond, a —CH$_2$—, —CH$_2$CH$_2$—, —CH$_2$OCH$_2$—, —CH$_2$OPhOCH$_2$— group, where Ph is a benzyl, ☐ represents a solid support, D is a protective group of the alcohols, W is selected from the C1-C12 alkane triyl groups, the C6-C18 aryl triyl groups and the C6-C18 aralkane triyl groups, Z is selected from the C1-C12 alkoxy groups, oxygen-containing or nitrogen-containing C3-C12 cycloheteroalkyl groups, C1-C12 NCO-alkyl groups, C1-C12 CON-alkyl groups, Y is selected from the linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups, X is selected from the linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups, R is selected from the C1-C12 acyl, C1-C12 S-alkyl, C6-C12 S-aryl, S-2-pyridine, oxygen-containing or nitrogen-containing C1-C12 S-heteroalkyl, C3-C12 S-cycloalkyl, oxygen-containing or nitrogen-containing C3-C12 S-cycloheteroalkyl groups.

According to an embodiment, the compound corresponds to one of the formulas (Ia), (Ib) and (Ic) below:

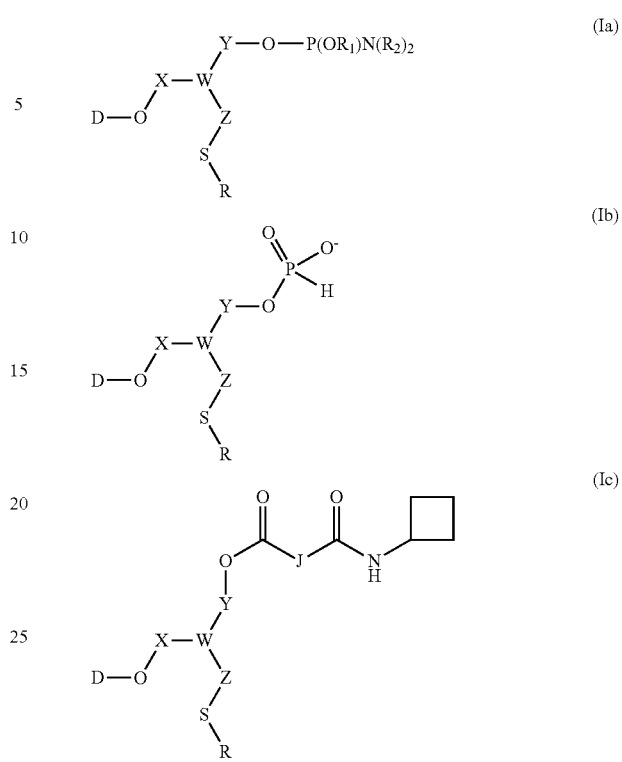

According to an embodiment,

D is selected from 4,4'-dimethoxytrityl, 9-phenylxanthen-9-yl or fluorenylmethoxycarbonyl;

W is selected from the C1-C6 alkane triyl groups, a C6-C12 aryl triyl group, a C6-C12 aralkane triyl group, more particularly from the CH, CCH$_3$, CCH$_2$CH$_3$, the cyclohexane triyl and the benzene triyl groups; and/or Z is selected from the C1-C6 alkoxy groups, oxygen-containing or nitrogen-containing C3-C6 cycloheteroalkyl groups, C1-C6 NCO-alkyl groups, C1-C6 CON-alkyl groups; and/or Y is selected from the linear or branched C1-C6 alkyl groups, C1-C6 aminoalkyl groups, C1-C6 alkoxy groups, C3-C6 cycloalkyl groups, oxygen-containing or nitrogen-containing C3-C6 cycloheteroalkyl groups; and/or X is selected from the linear or branched C1-C6 alkyl groups, C1-C6 aminoalkyl groups, C1-C6 alkoxy groups, C3-C6 cycloalkyl groups, oxygen-containing or nitrogen-containing C3-C6 cycloheteroalkyl groups; and/or R is selected from the C1-C6 acyl, C1-C6 S-alkyl, C6-C6 S-aryl, oxygen-containing or nitrogen-containing C1-C6 S-heteroalkyl, C3-C6 S-cycloalkyl, oxygen-containing or nitrogen-containing C3-C6 S-cycloheteroalkyl groups, preferably R is a C1-C6 acyl group.

According to an embodiment, T is a group —O—P(OR$_1$)N(R$_2$)$_2$ where R$_2$ is an isopropyl group and R$_1$ is chosen from 2-cyanoethyl, 2-(trimethylsilyl)ethyl, 2-(triphenylsilyl)ethyl, 2-(diphenylmethylsilyl)ethyl groups.

According to an embodiment, T is a group —OC(O)JC(O)NH-☐ where ☐ is a solid support selected from resins, in particular from resins based on polystyrene, polyacrylamide, polyethyleneglycol, cellulose, polyethylene, polyester, latex, polyamide, polydimethylacrylamide, hydrophilic natural or synthetic polymers, glass beads, silica gels.

Another object of the present invention is a manufacturing process of a compound of formula (I) according to the present invention, comprising at least one step selected from the following steps:

Preparation of the compound (Ia) starting from compound (II) according to the following synthesis diagram:

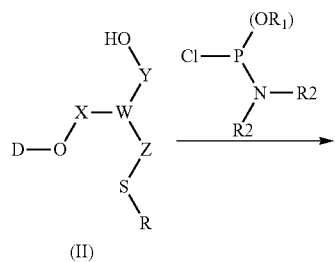

or according to the following synthesis diagram:

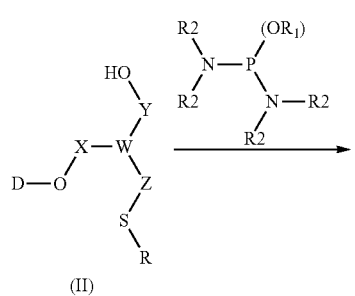

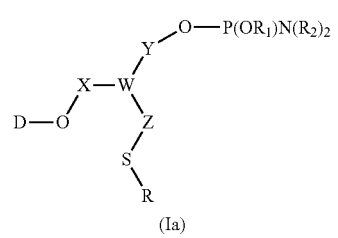

Preparation of the compound (Ib) starting from compound (II) according to the following synthesis diagram:

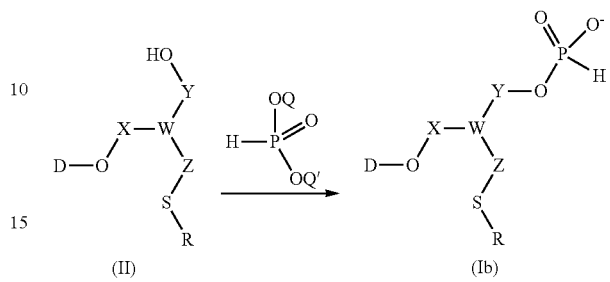

in which Q and Q' represent, independently of one another, a substituted or unsubstituted benzene group, Preparation of the compound (Ic) starting from compound (II) according to the following synthesis diagram:

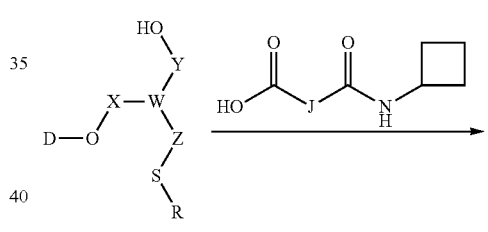

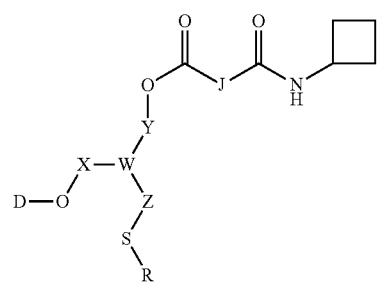

or according to the following synthesis diagram:

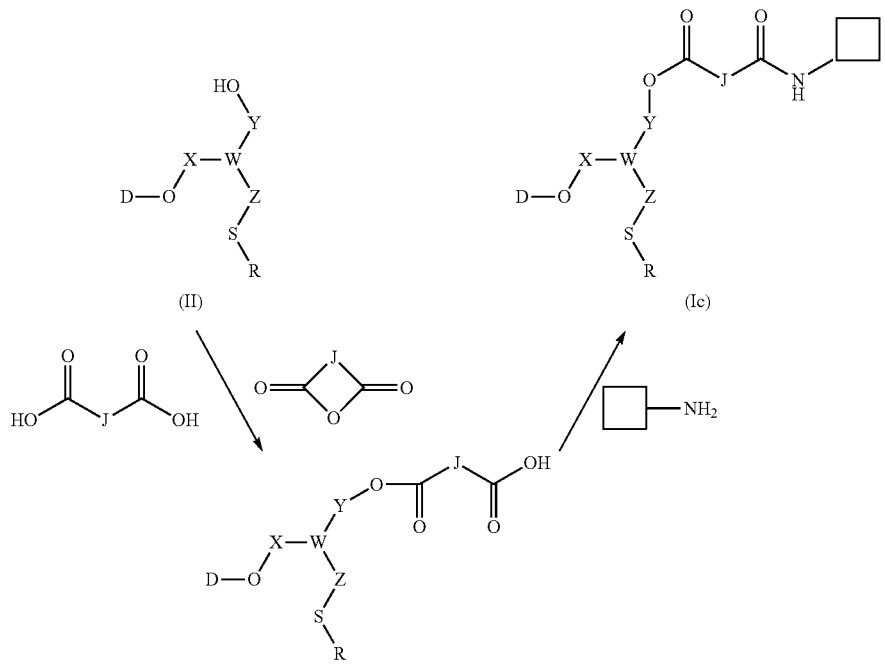

D, X, Y, Z, W, R, □, R1 and R2 having the same definition in each of these steps as in compound (I).

Another object of the present invention is an oligomer obtainable by oligomerization of a compound (I) according to the invention, having the formula:

(Ic)-(Δ)$_k$     (XVI)$_k$ in which:

(Ic) has the same meaning as above, R group of compound (Ic) can further represent H, k represents an integer between 1 and 12, (Δ) represents (I'a) or (I'b), with:

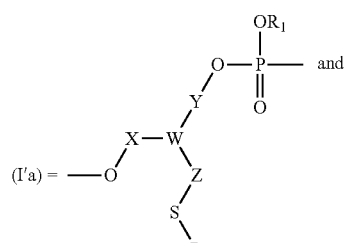

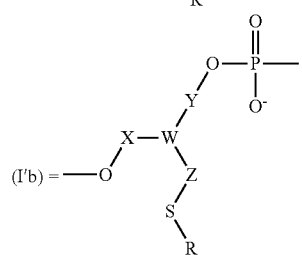

in which X, Y, W, Z, R, 1 have the same definition as in compound (I), R can further represent H.

According to an embodiment, the oligomer according to the invention has the formula (XIV)$_k$:

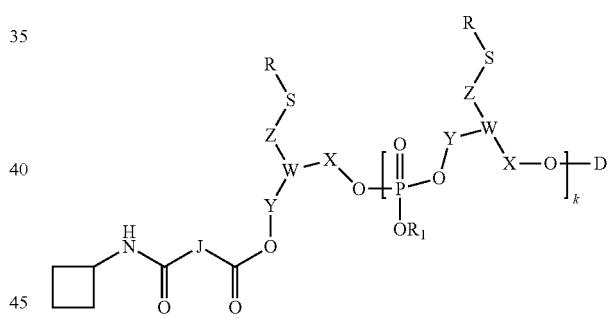

in which:

□, D, X, Y, W, Z, R and R$_1$ have the same definition as for compound (I), R can further represent H and D can further represent H, k is an integer comprised between 1 and 11.

The invention also relates to a process for manufacturing a modified oligomer comprising at least:
- a step of grafting a compound (I) according to the invention on an oligonucleotide, or
- a step of grafting a nucleotide on an oligomer according to the invention.

Another object of the invention is an oligonucleotide modified, obtainable by the process according to the invention, having the following formula (XIIa):

□-N$_1$—N$_2$— . . . —N$_{n-1}$—N$_n$—(I')$_y$-(M$_1$- . . .
-M$_{m-1}$-M$_m$)$_p$-(I')$_{y'}$ in which, N$_1$, . . . N$_n$ represent, independently of one another, a nucleotide, M$_1$, . . . M$_m$ represent, independently of one another, a nucleotide, (I') represents a compound of formula (I' a) or (I' b) as defined above, n is an integer comprised between 1 and 100, m is an integer comprised between 1 and 100, y is an integer comprised between 1 and 12, p represents 0 or 1, y' is an integer comprised between 0 and 12 if p has the value 1, and y' is equal to 0 if p has the value 0, ☐ represents a solid support.

Another object of the invention is an oligonucleotide modified, obtainable by the process according to the invention, having the following formula (XIIIa):

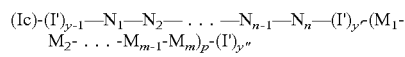

in which, $N_1, \ldots N_n$ represent, independently of one another, a nucleotide, $M_1, \ldots M_m$ represent, independently of one another, a nucleotide, (I') represents a compound of formula (I' a) or (I' b) as defined above, n is an integer comprised between 1 and 100, m is an integer comprised between 1 and 100, y is an integer comprised between 1 and 12, y' is an integer comprised between 0 and 12, p has the value 0 or 1 if y' is different from 0, and if y' has the value 0 then p has the value 0, y" is an integer comprised between 0 and 12 if p has the value 1, and if p has the value 0 then y" has the value 0.

According to an embodiment, the modified oligonucleotide according to the invention has the formula (XIIc):

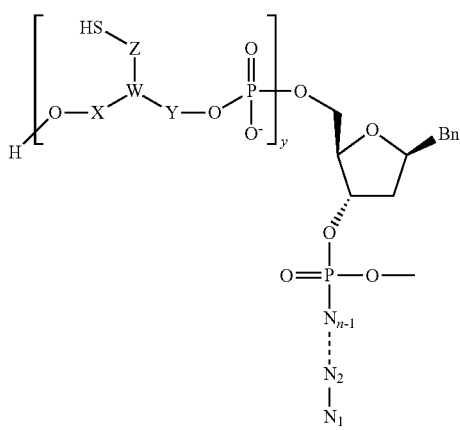

in which, $n, y, N_1, \ldots N_{n-1}$, have the same definition as above,

X, Y, Z, W have the same definition as above,

Bn represents the base of the $n^{th}$ nucleotide.

According to an embodiment, the modified oligonucleotide according to the invention has the formula (XIIIc):

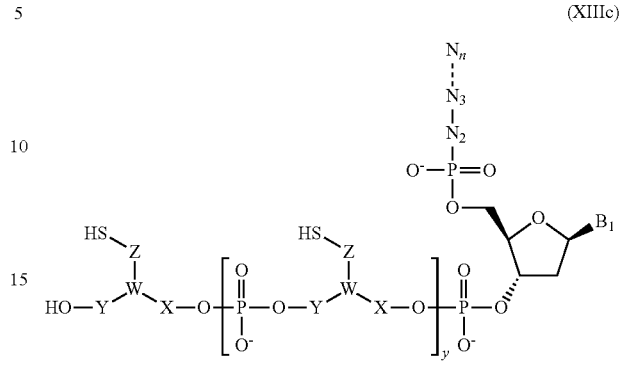

in which, n, y, N have the same definition as above,

X, Y, Z, W have the same definition as above,

B1 corresponds to the base of the first nucleotide.

Another object of the invention relates to an automated device for the synthesis of nucleotides comprising at least distinct containers containing Nucleotides, Coupling activators and washing products, mechanical means for sampling and distribution of product samples, as well as computer means for the controlled implementation of these mechanical means, and:

at least one container in which is placed a solid support grafted with an oligomer according to the invention and/or at least one container containing a compound (Ia) or a compound (Ib) according to the invention.

The invention further relates to a substrate grafted with at least one modified oligonucleotide according to the invention, said substrate comprising at least one receiving zone coated with a gold or platinum film or grafted with groups comprising at least one carbon-carbon double bond or a carbon-carbon triple bond or haloacetamide groups, preferably maleimide or acrylamide groups, said substrate being in metal in case of gold film and in plastic in case of grafting with groups comprising at least one carbon-carbon double bond or a carbon-carbon triple bond or haloacetamide groups, preferably maleimide or acrylamide groups.

According to an embodiment of the invention, the groups comprising at least one carbon-carbon double bond or a carbon-carbon triple bond are chosen from alkenes activated by a carbonyl function in alpha position, preferably the alkenes are chosen from maleimide, acrylamide groups.

According to an embodiment, the haloacetamide groups are chosen from bromoacetamido and iodoacetamido groups.

According to an embodiment of the invention, the groups comprising at least one carbon-carbon triple bond are chosen from alkynes activated by a carbonyl function in alpha, preferably alkynes are chosen from 2-propynamide groups.

According to an embodiment, the metal substrate is in copper or in titanium and/or the plastic substrate is in polystyrene.

The present invention also proposes a test kit comprising:

at least one substrate comprising at least one receiving zone coated with a gold or platinum metallic film or a substrate grafted with groups comprising at least one carbon-carbon double bond or a carbon-carbon triple bond or haloacetamide groups, preferably maleimide or acrylamide groups, at least one modified oligonucleotide according to the invention.

Another object of the invention relates to the use of a substrate according to the invention to produce affinity tests between an oligonucleotide and another molecule.

Another object of the invention relates to the use of a compound comprising at least two thiol groups for grafting of oligonucleotides on a surface modified with groups comprising at least one carbon-carbon double bond or carbon-carbon triple bond or haloacetamide groups, preferably maleimide or acrylamide groups for the establishment of a diagnostic test.

The advantages of the present invention are the followings:

the thiol compound of the invention is inexpensive,
the thiol compound of the invention is obtained by a method which is simple to implement,
the thiol compound of the invention may be introduced one or more times in an oligonucleotide in a simple and efficient manner,
the grafted oligonucleotide of the invention can be stably immobilized on a gold surface, or on a grafted, notably with acrylamide or maleimide groups, surface,
the oligonucleotides of the invention can be manufactured by a fully automated process.

Other features and advantages of the invention will become apparent on reading the following description of a preferred embodiment of the invention, given as an example, and referring to the attached drawings.

BRIEF DESCRIPTION OF THE DRAWINGS

FIG. 13b shows the reactions between the modified oligonucleotide according to the invention and the surface grafted with alkenyl or alkynyl groups with activation by light ($\lambda$=265 nm).

DISCLOSURE OF EMBODIMENTS OF THE INVENTION

Figure 1:
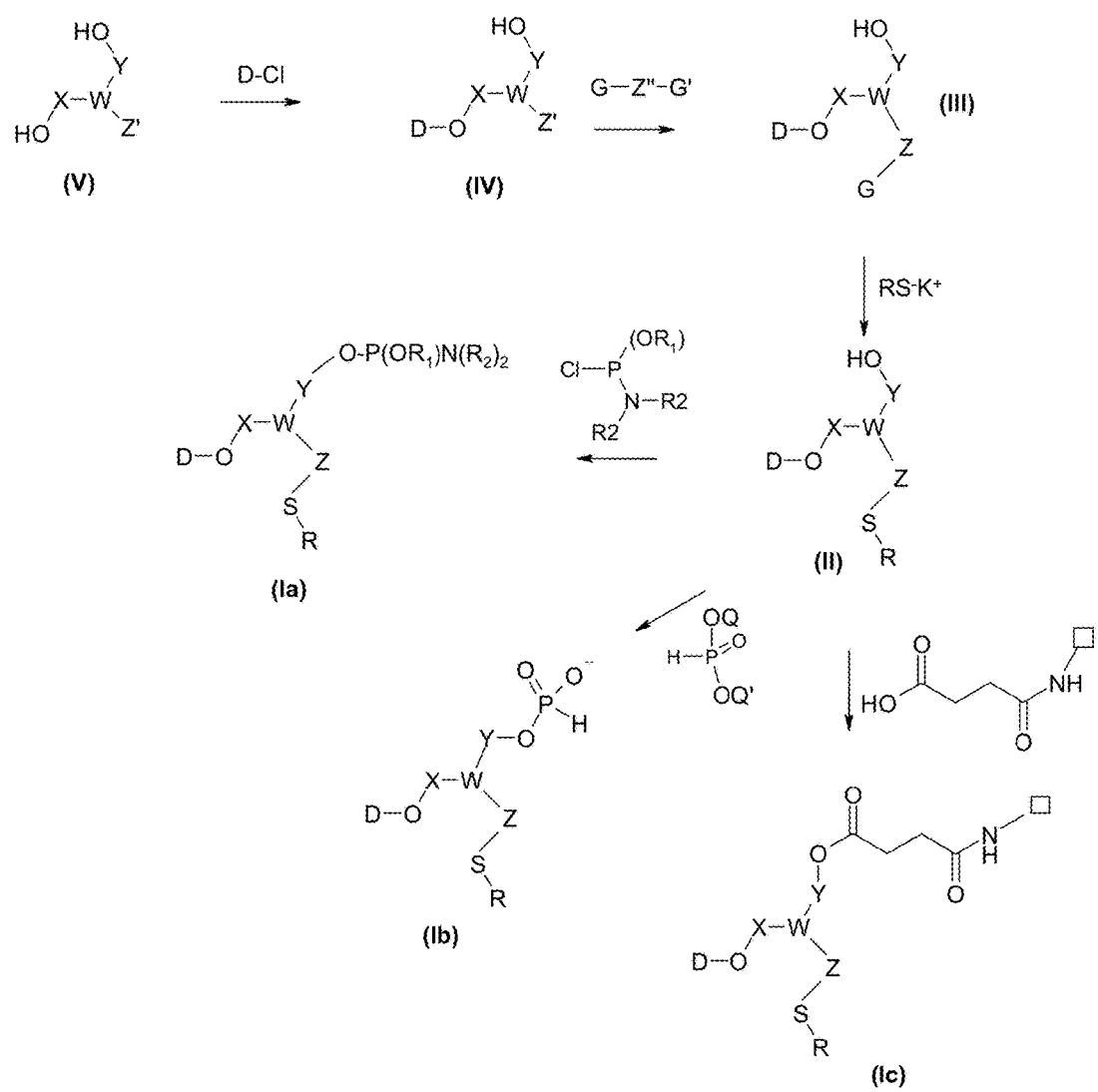
FIG. 1 shows a diagram describing a method of synthesis of compounds (I).

The present invention relates to the preparation and the use of compounds of phosphoramidite, H-phosphonate structure or of compounds bound to a solid support having a protected thiol function. These thiol compounds are intended to be introduced into oligonucleotides. The oligonucleotides thus obtained may have several thiol functions.

Thiol Compound

The compounds of the present invention correspond to the following formula (I):

in which:

T is a group selected from —O—P(OR$_1$)N(R$_2$)$_2$, —O—PH(O)O$^-$, —OC(O)JC(O)NH-□, R$_1$ is selected from the 2-cyanoethyl, R'$_1$R'$_2$R'$_3$SiCH$_2$CH$_2$, groups and R'$_1$, R'$_2$, R'$_3$, which may be identical or different, represent a group selected from the linear or branched alkyls comprising from 1 to 12 carbon atoms and the C6-C12 aryls, R$_2$ is selected from the linear or branched alkyl groups comprising from 1 to 12 carbon atoms, pyrrolidine, J is selected from a single bond, a —CH$_2$—, —CH$_2$CH$_2$—, —CH$_2$OCH$_2$—, —CH$_2$OPhOCH$_2$— group, where Ph is a benzyl, □ represents a solid support, D is a protective group of the alcohols, W is selected from the C1-C12 alkane triyl groups, the C6-C18 aryl triyl groups and the C6-C18 aralkane triyl groups, Z is selected from the C1-C12 alkoxy groups, oxygen-containing or nitrogen-containing C3-C12 cycloheteroalkyl groups, C1-C12 NCO-alkyl groups, C1-C12 CON-alkyl groups, Y is selected from the linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups, X is selected from the linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups, R is selected from the C1-C12 acyl, C1-C12 S-alkyl, C6-C12 S-aryl, S-2-pyridine, oxygen-containing or nitrogen-containing C1-C12 S-heteroalkyl, C3-C12 S-cycloalkyl, oxygen-containing or nitrogen-containing C3-C12 S-cycloheteroalkyl groups.

Within the meaning of the present invention, by "alkane triyl" is meant the linear, branched or cyclic alkane triyls, optionally substituted with one or more alkyl groups.

Among the aryl triyl groups that may be present in the compound according to the invention, there may be mentioned benzene triyl and naphthalene triyl.

Among the aralkane groups, there may be mentioned 1,3,5-trimethylbenzene triyl and trimethylnaphthalene triyl.

Compound (I) may be divided into three sub-compounds (Ia), (Ib) and (Ic) corresponding to the following formulae (Ia), (Ib) and (Ic), in which the parameters X, Y, Z, R, $R_1$, $R_2$ and D have the same definition as presented above for formula (I):

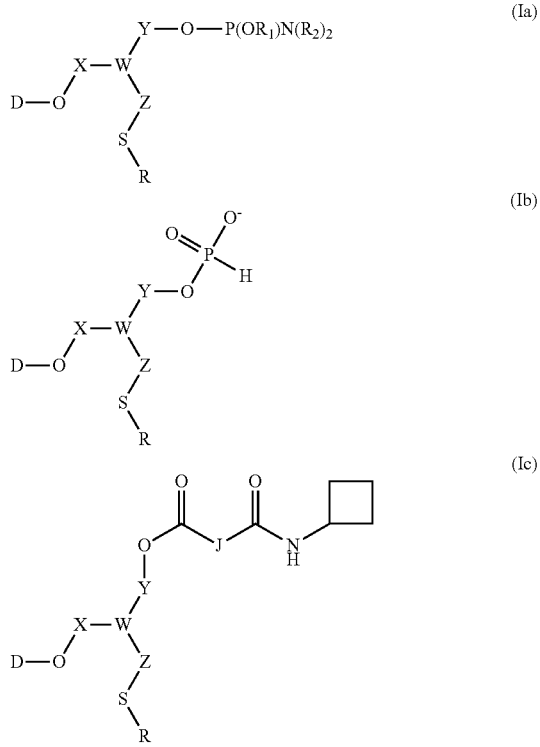

Preferably, $R_1$ is selected from the 2-cyanoethyl and $R'_1R'_2R'_3SiCH_2CH_2$ groups, and $R'_1$, $R'_2$, $R'_3$, which may be identical or different, represent a group selected from the linear or branched alkyl groups comprising from 1 to 6 carbon atoms, and phenyl; preferably $R_1$ is selected from the 2-cyanoethyl and $R'_1R'_2R'_3SiCH_2CH_2$ groups, and $R'_1$, $R'_2$, $R'_3$, which may be identical or different, represent a group selected from the linear or branched alkyl groups comprising from 1 to 3 carbon atoms, and phenyl; even more preferably $R_1$ is selected from the 2-cyanoethyl, 2-(trimethylsilyl)ethyl, 2-(triphenylsilyl)ethyl, 2-(diphenylmethylsilyl)ethyl groups.

Preferably, $R_2$ is selected from the linear or branched alkyl groups comprising from 1 to 6 carbon atoms. Preferably, $R_2$ is an isopropyl group (iPr).

Preferably, the solid support is selected from the resins, in particular from the resins based on polystyrene, polyacrylamide, polyethylene glycol, cellulose, polyethylene, polyester, latex, polyamide, polydimethylacrylamide, synthetic or natural hydrophilic polymers, glass beads, silica gels.

Preferably, W is selected from the C1-C6 alkane triyl groups, a C6-C12 aryl triyl group, a C6-C12 aralkane triyl group, more particularly from the CH, $CCH_3$, $CCH_2CH_3$ groups, the cyclohexane triyl and the benzene triyl.

Preferably, D is selected from the protective groups of the alcohols that allow orthogonal deprotection with respect to the other groups of compound (I). More particularly, D is selected from 4,4'-dimethoxytrityl (DMTr), 9-phenylxanthen-9-yl (pixyl) or fluorenylmethoxycarbonyl (Fmoc). The pixyl protective group is described in particular in the document Chattopadhyaya and Reese, *Chem. Soc. Chem. Comm.*, 1978, 639-640. Another possible protective group of the alcohols is a tert-butyl-dimethylsilyl group, and in this case a polystyrene support will be particularly preferred.

Preferably, Z is selected from the C1-C6 aminoalkyl, C1-C6 alkoxy, oxygen-containing or nitrogen-containing C3-C6 cycloheteroalkyl, C1-C6 NCO-alkyl, C1-C6 CON-alkyl groups.

Preferably, Y is selected from the linear or branched C1-C6 alkyl groups, C1-C6 aminoalkyl, C1-C6 alkoxy, C3-C6 cycloalkyl, oxygen-containing or nitrogen-containing C3-C6 cycloheteroalkyl groups.

Preferably, X is selected from the linear or branched C1-C6 alkyl groups, C1-C6 aminoalkyl, C1-C6 alkoxy, C3-C6 cycloalkyl, oxygen-containing or nitrogen-containing C3-C6 cycloheteroalkyl groups.

Preferably, R is selected from the C1-C12 acyl, C1-C6 S-alkyl, C6 S-aryl, oxygen-containing or nitrogen-containing C6 S-heteroalkyl, C6 S-cycloalkyl, oxygen-containing or nitrogen-containing C6 S-cycloheteroalkyl groups.

According to an embodiment, the linear or branched alkyls are selected from the methyl, ethyl, propyl, butyl, pentyl, hexyl, heptyl, octyl, nonyl, decyl, undecyl, dodecyl, isopropyl, isobutyl, tert-butyl groups.

According to an embodiment, the aminoalkyls are selected from the aminomethyl, aminoethyl, aminopropyl, aminobutyl, aminopentyl, aminohexyl, aminoheptyl, aminooctyl, aminononyl, aminodecyl, aminoundecyl, aminododecyl, aminoisopropyl, aminoisobutyl, amino-tert-butyl groups comprising one or more nitrogen atoms.

According to an embodiment, the alkoxys are selected from the methoxy, ethoxy, propyloxy, oxybutyloxy, pentyloxy, hexyloxy, heptyloxy, octyloxy, nonyloxy, decyloxy, undecyloxy, dodecyloxy, isopropyloxy, isobutyloxy, tert-butyloxy groups comprising one or more oxygen atoms.

According to an embodiment, the cycloalkyls are selected from the rings, optionally comprising one or more unsaturations, comprising between 3 and 12 carbon atoms, preferably 6 carbon atoms.

According to an embodiment, the cycloheteroalkyls are selected from the rings substituted with one or more nitrogen and/or oxygen atoms, optionally comprising one or more unsaturations and comprising between 3 and 12 carbon atoms, preferably 5 carbon atoms and one nitrogen or oxygen atom.

According to an embodiment, the NCO-alkyls and CON-alkyls are groups in which the alkyls may be linear or branched alkyls selected from methyl, ethyl, propyl, butyl, pentyl, hexyl, heptyl, octyl, nonyl, decyl, undecyl, dodecyl, isopropyl, isobutyl, tert-butyl groups.

According to an embodiment, $R_2$ is an isopropyl group (iPr) and/or $R_1$ is a cyanoethyl group.

According to a preferred embodiment, the thiol compound (Ia) is compound (VI) corresponding to the following formula:

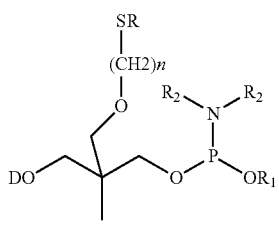
(VI)

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

According to another embodiment, the thiol compound (Ia) is compound (VII) corresponding to the following formula:

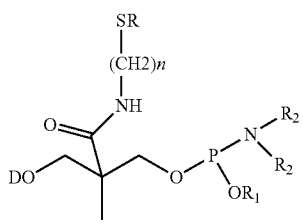
(VII)

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

According to an embodiment, the thiol compound (Ic) is compound (VIII) corresponding to the following formula:

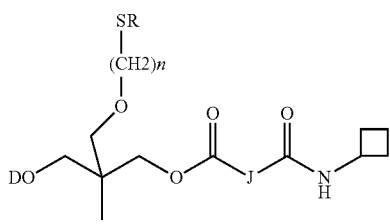
(VIII)

in which, n is an integer between 1 and 12, preferably between 1 and 6,

R, D and □ have the same definition as above for (Ic).

Preferably, R is an acetyl group. Preferably, J is an ethyl group. Preferably, D is 4,4'-dimethoxytrityl.

According to an embodiment, the thiol compound (Ia) is compound (IX) of formula:

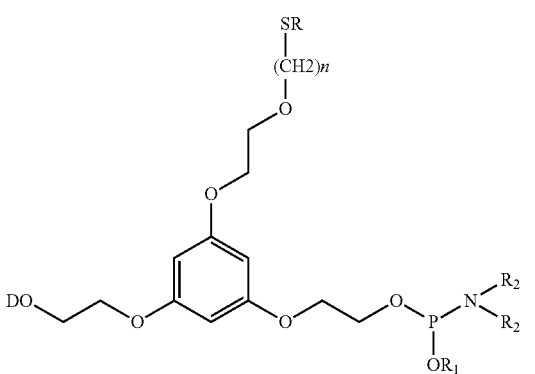
(IX)

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

According to an embodiment, the thiol compound (Ia) is compound (X) of formula:

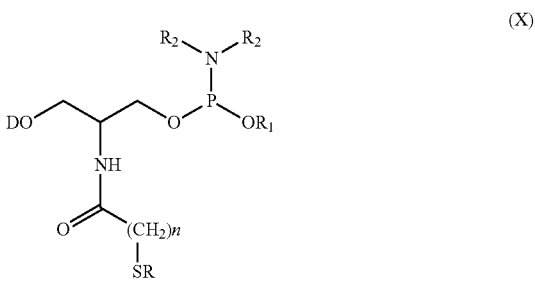
(X)

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

Preferably, $R_2$ is an isopropyl group (iPr) and $R_1$ is a cyanoethyl group.

According to an embodiment, the thiol compound (Ia) is compound (XI) of formula:

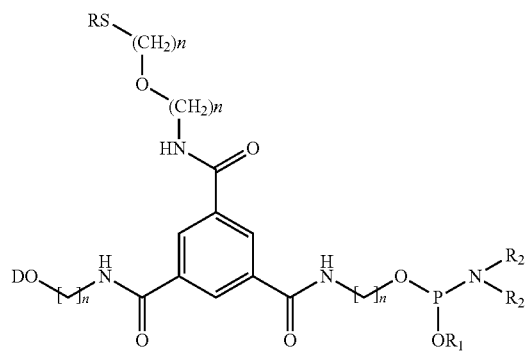

(XI)

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

Manufacturing Process

The manufacturing process of compounds (Ia), (Ib) and (Ic) is represented in the diagram in FIG. 1.

Compounds (Ia), (Ib) and (Ic) are obtained from the same compound (II) having the following formula:

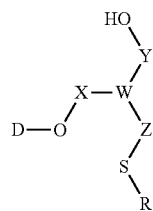

(II)

in which D, X, W, Y, Z and R have the same definition as in the thiol compound (I).

The compound of formula (Ia) may be obtained by the reaction represented in the following diagram:

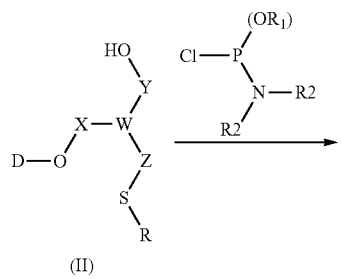

(II)

-continued

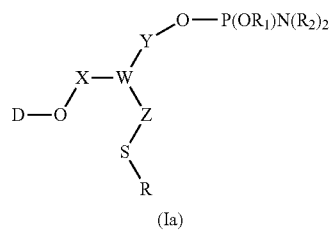

(Ia)

or by the reaction represented in the following diagram, preferably in the presence of the salt of diisopropylamine tetrazolide:

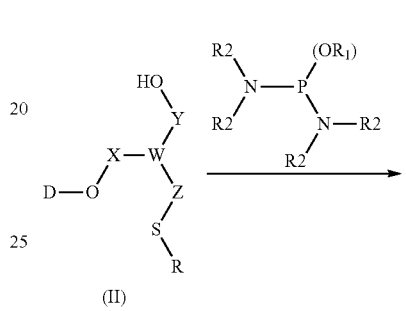

(II)

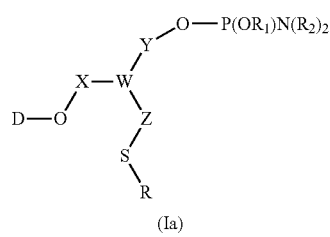

(Ia)

The compound of formula (Ib) may be obtained by the reaction represented in the following diagram:

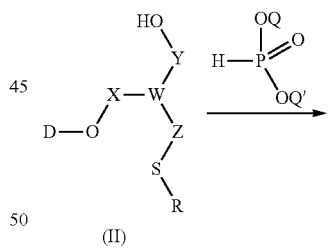

(II)

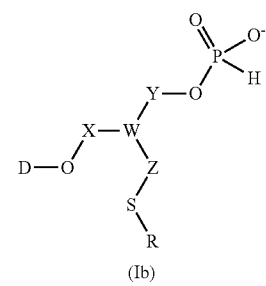

(Ib)

in which Q and Q' represent, independently of one another, a substituted or unsubstituted benzene group.

The foregoing reaction for obtaining compound (Ia) or (Ib) is carried out starting from compound (II), preferably in the presence of a base, for example diisopropylethylamine (DIEA), in an anhydrous solvent, such as anhydrous dichloromethane.

The compound of formula (Ic) is also obtained from compound (II) but preferably according to the reaction step represented in the following diagram:

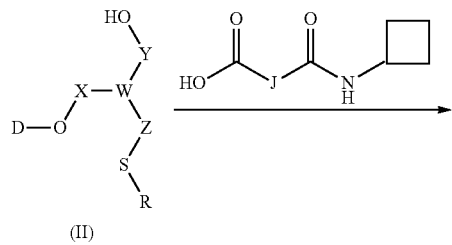

(II)

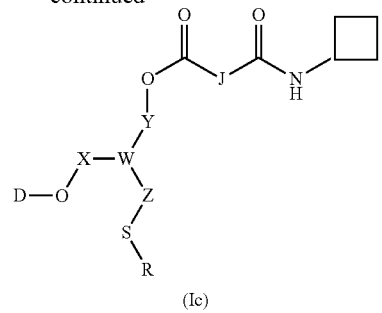

(Ic)

The preceding reaction for obtaining compound (Ic) is preferably carried out in an anhydrous solvent, such as pyridine, in the presence of a base, such as triethylamine It is also possible to obtain compound (Ic) according to the following reaction diagram:

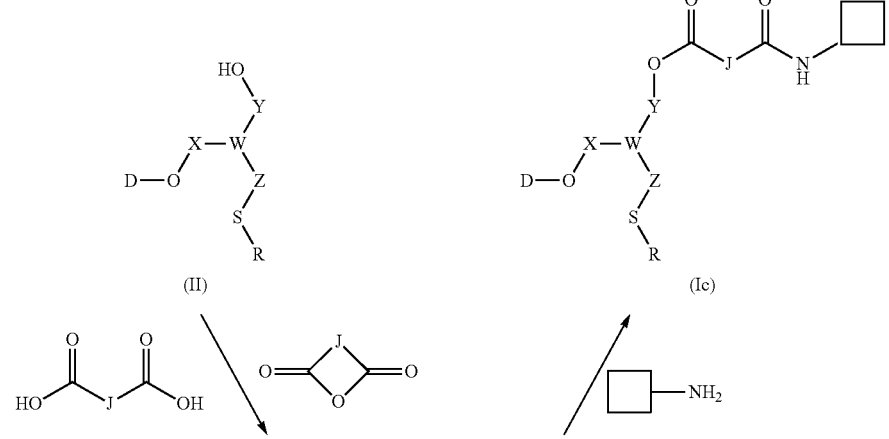

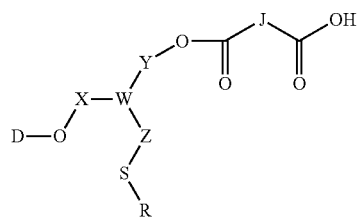

An object of the present invention is the compound (II) of the above formula, in which the D, X, W, Z, Y and R groups have the same definition as in compound (I).

The compound of formula (II) may be obtained from compound (III) according to the reaction step described below:

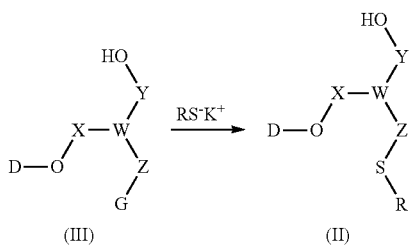

(III) → (II)

in which G is a halogen, preferably bromine or iodine.

The reaction described above is preferably carried out in an anhydrous solvent, such as anhydrous toluene and in the presence of a crown ether.

Compound (III) may be obtained from compound (IV) according to the reaction step described below:

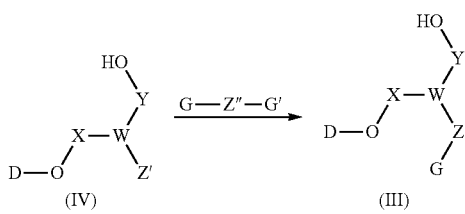

(IV) → (III)

in which,

G and G' are halogen atoms, which may be identical or different, preferably G and G' are bromine or iodine atoms, Z' is a C1-C12 aminoalkyl, C1-C12 alkoxy, oxygen-containing or nitrogen-containing C3-C12 cycloheteroalkyl, C1-C12 NCO-alkyl, C1-C12 CON-alkyl group, Z" is a C1-C12 linear or branched alkyl, C1-C12 aminoalkyl, C1-C12 alkoxy, C3-C12 cyclo alkyl, oxygen-containing or nitrogen-containing C3-C12 cycloheteroalkyl, C1-C12 NCO-alkyl, C1-C12 CON-alkyl group, the dihalogenated compound G-Z"-G' being intended to react with the Z' group of compound (IV) to lead to the formation of the Z-G group of compound (III).

The step of obtaining compound (III) is preferably carried out in the presence of an alkali hydride, such as NaH.

Compound (IV) may be obtained from the commercial compound (V) by protection of the alcohol function, according to the following reaction step:

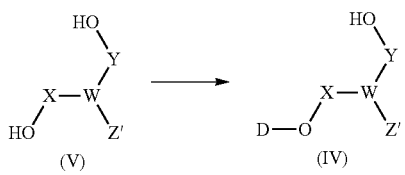

(V) → (IV)

This step of protection of the alcohol function is carried out under conditions well known to a person skilled in the art, depending on the choice of D.

According to an embodiment, compound (IV) is obtained from compound (V) by reaction with 4,4'-dimethoxytrityl chloride (DMTr-Cl) preferably in a solvent, such as pyridine in order to protect the alcohol function.

According to another embodiment, compound (IV) is obtained from compound (V) starting from 9-phenylxanthen-9-yl chloride (pixyl-Cl) under the conditions described in the document Chattopadhyaya and Reese, *Chem. Soc. Chem. Comm.*, 1978, 639-640.

According to another embodiment, compound (IV) is obtained from compound (V) by reaction with fluorenylmethoxycarbonyl chloride (Fmoc-Cl) under conditions well known to a person skilled in the art.

In the above formulae (II) to (V), X, Y, W, Z, D, R, $R_1$, $R_2$ have the same definitions as in the definition of compound (I) given above.

Preferably, the starting compound (V) is 1,1,1-tris(hydroxymethyl)ethane or 2,2-bis(hydroxymethyl)propionic acid or 1,3,5-tris(hydroxyethoxy)benzene or 1,3,5-tris(hydroxymethyl)cyclohexane or 2-amino-1,3-propanediol.

Oligomer of the Thiol Compound

Figure 2A:
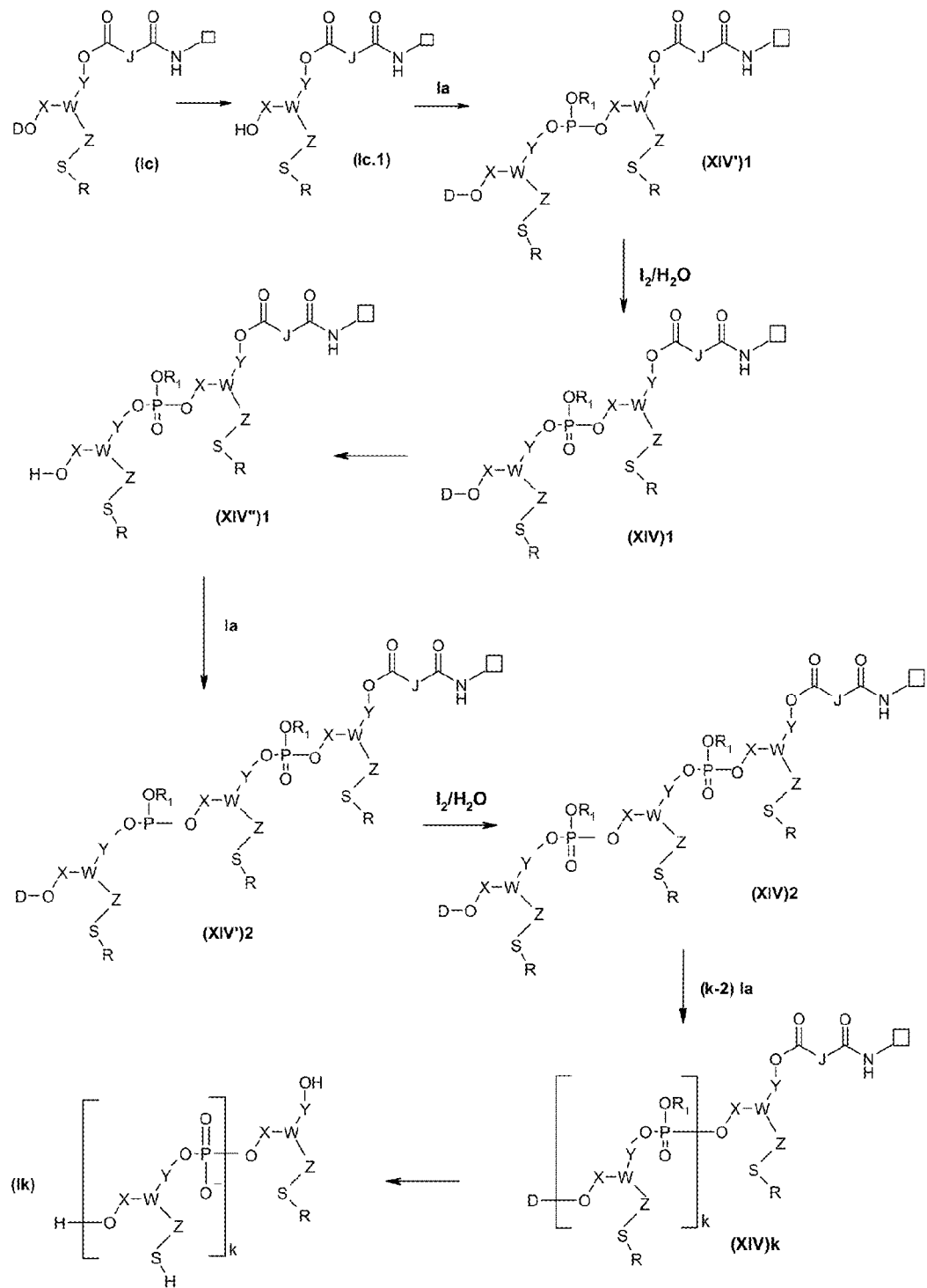
FIGS. 2A and 2B show, respectively, a diagram describing a method of synthesis of an oligomer of the compounds of the invention starting from compounds (Ia) and starting from compounds (Ib).
Figure 2B:
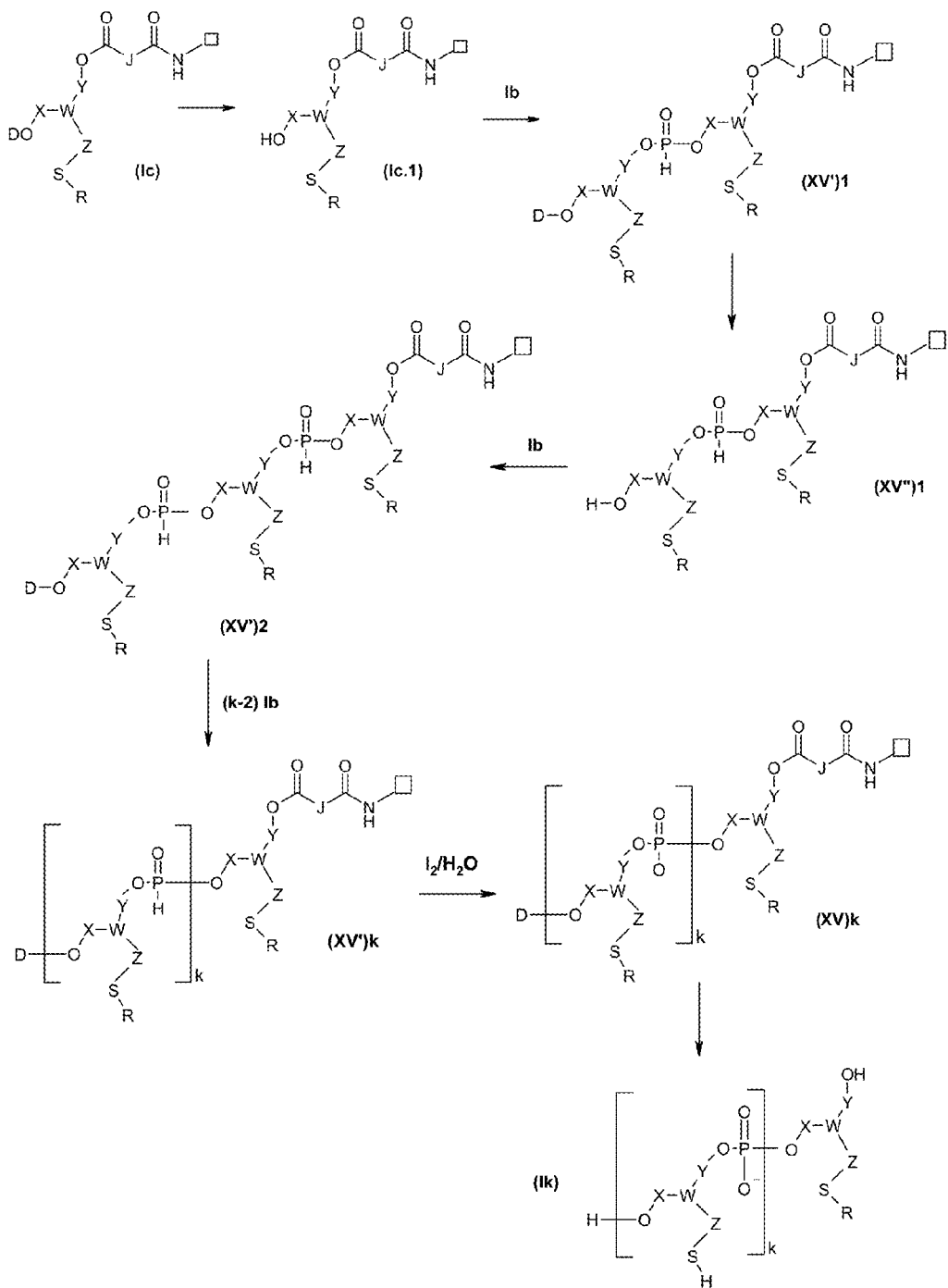

An object of the present invention relates to an oligomer formed from thiol compounds of formula (I) described above. The method of synthesis of these oligomers is described in the diagram in FIG. 2A for the oligomerization of compounds of formula (Ia) and in the diagram in FIG. 2B for the oligomerization of compounds of formula (Ib).

In a first step, the alcohol function of compound (Ic) is deprotected in order to lead to compound (Ic.1). This deprotection step is carried out by means that are well known to a person skilled in the art, preferably in the presence of di- or trichloroacetic acid for the groups DMTr and Pixyl and of piperidine for the Fmoc group.

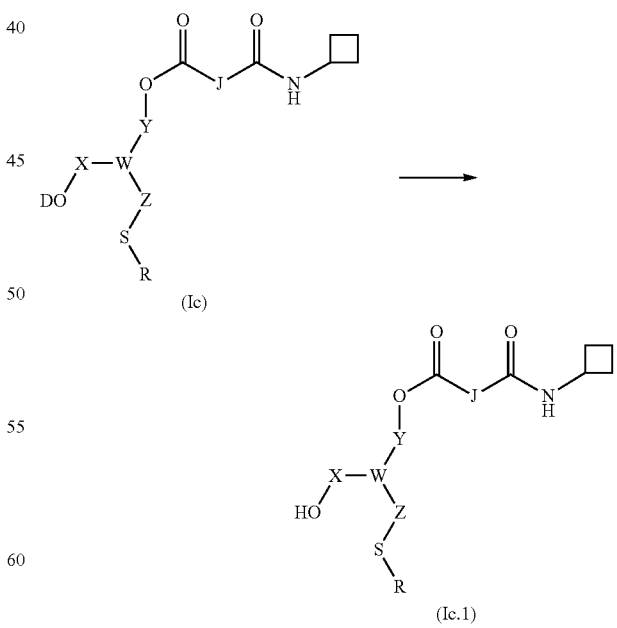

(Ic)

(Ic.1)

Then, compound (Ic.1) reacts with compound (Ia) or (Ib), leading respectively to the compound phosphite triester (XIV')1 or H-phosphonate diester (XV')1.

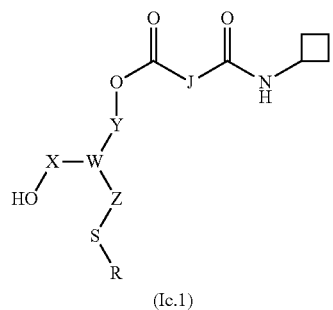

(Ic.1)

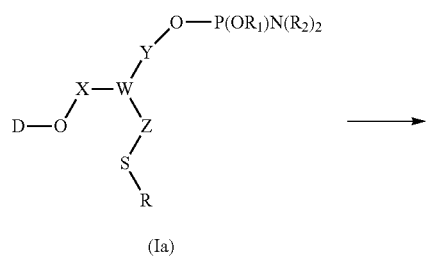

(Ia)

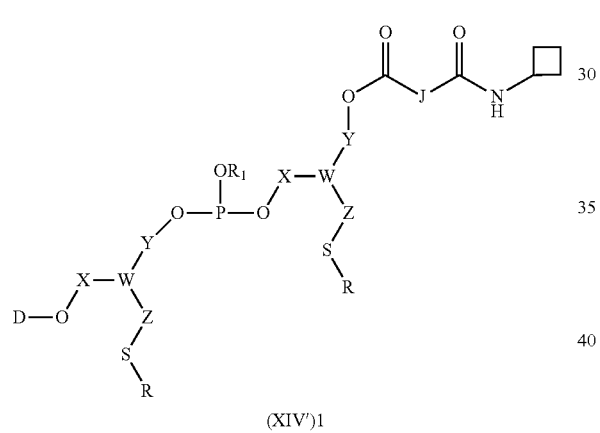

(XIV')1

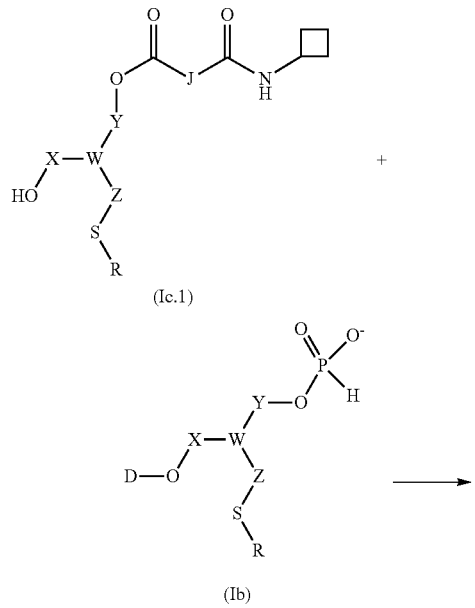

(Ib)

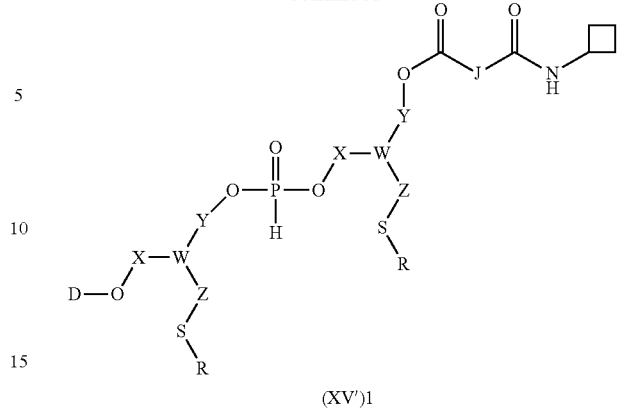

(XV')1

Then, compound (XIV')1 is oxidized preferably in the presence of diiodine, the diiodine then being displaced by water supplying the oxygen atom of the phosphate triester bond, leading to the phosphotriester compound (XIV)1. This oxidation step is carried out after each coupling step between a compound (XIV)i and a compound (Ia).

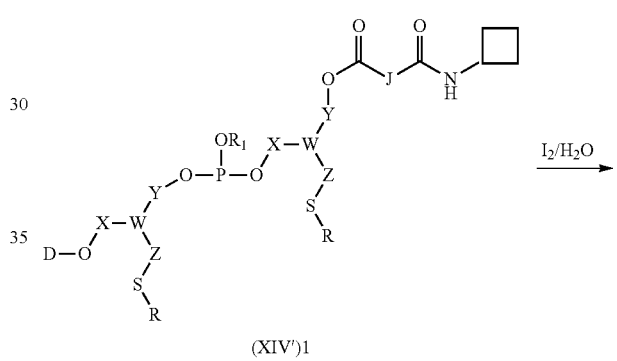

(XIV')1

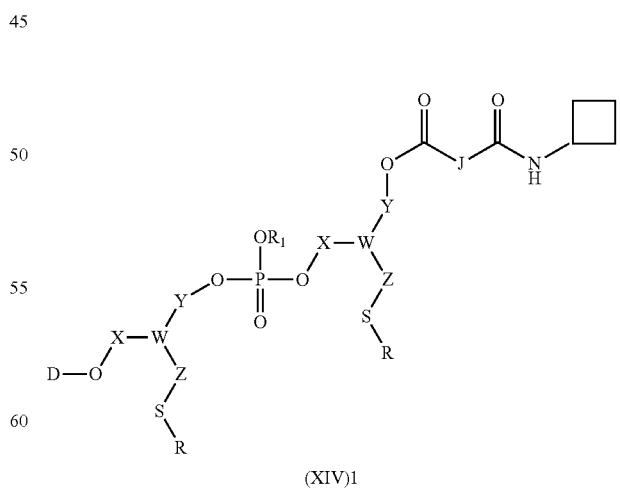

(XIV)1

Then, in the same way, compound (XIV)1 reacts with (k-1) compounds (Ia), leading, after (k-1) oxidations, to compound $(XIV)_k$:

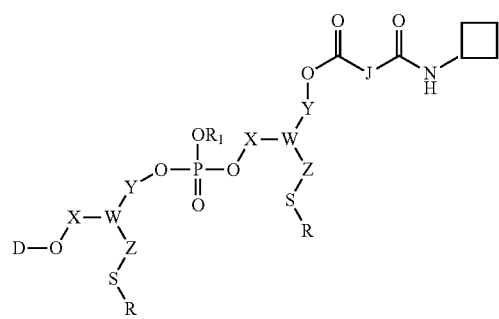
(XIV)1
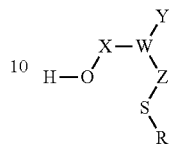
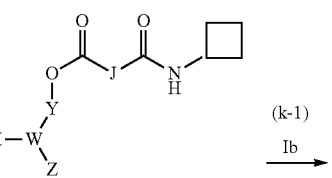
(XV")1
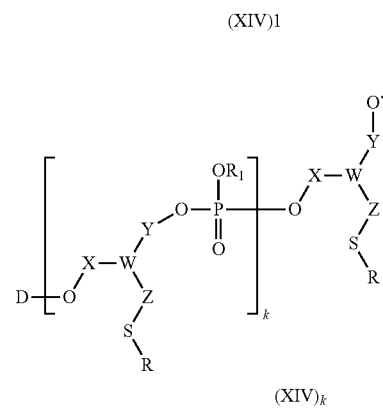
(XIV)$_k$
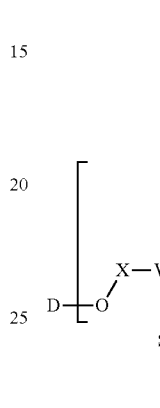
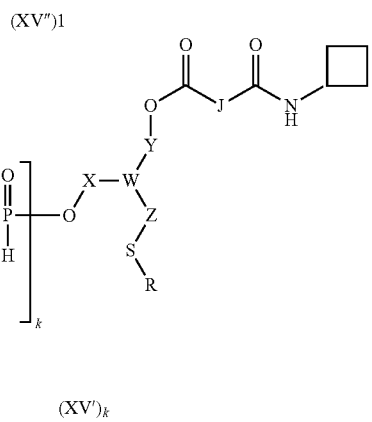
(XV')$_k$
and compound (XV')1 is deprotected on its alcohol function to give (XV")1, which reacts with (k-1) compounds (Ib), leading to compound (XV')$_k$:
Then, compound (XV')$_k$ is oxidized, preferably in the presence of diiodine and water, leading to the phosphodiester compound (XV)$_k$.
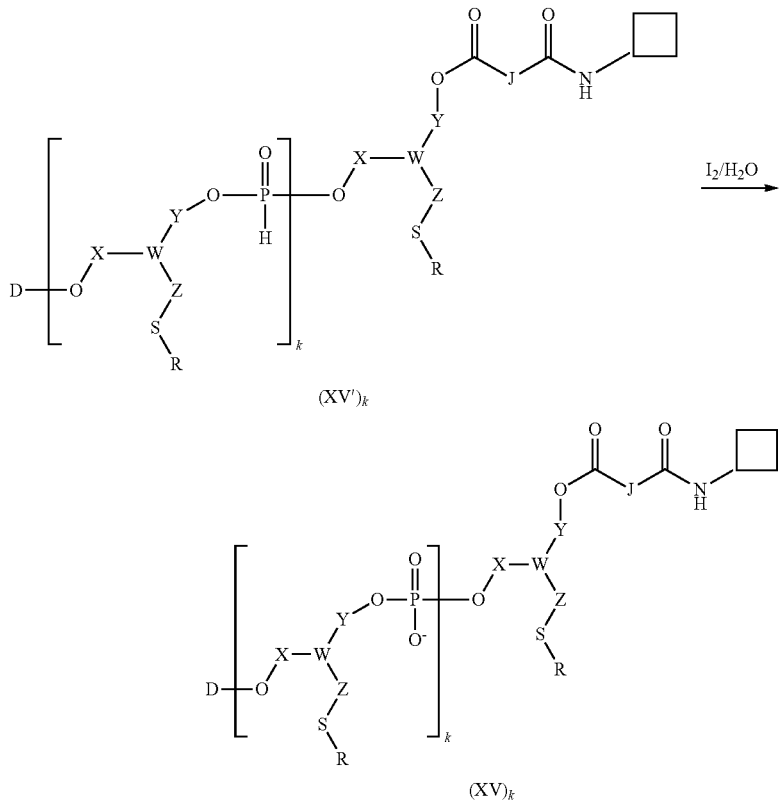
(XV')$_k$
(XV)$_k$ Finally, an optional last step consists of deprotecting compounds (XIV)$_k$ or (XV)$_k$, leading to the same compound (I)$_k$.

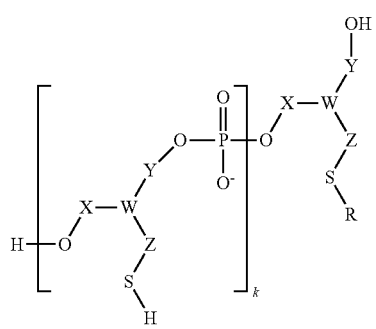

Preferably, the oligomer results from the oligomerization of 2 to 12 compounds (I), in particular between 2 and 8 compounds (I), i.e. the oligomer may comprise 2, 3, 4, 5, 6, 7 or 8 compounds (I). Preferably, the thiol oligomer intended to be grafted on a gold surface comprises between 3 and 8, advantageously between 4 and 8 compounds (I) and the thiol oligomer intended for conjugation with a substrate grafted with a group comprising at least one carbon-carbon double bond or carbon-carbon triple bond or a haloacetamide group, notably maleimide or acrylamide, comprises between 2 and 6 compounds (I).

According to an embodiment, the oligomer is produced solely from compounds of formula (Ia) or from compounds of formula (Ib). The oligomerization is carried out by reaction between the deprotected alcohol function of a first compound (I) and the phosphoramidite or H-phosphonate function of a second compound (I).

It is also possible to envisage production of an oligomer starting from a mixture of compounds (Ia) and of compounds (Ib), this embodiment being of less interest.

Preferably, the oligomer is produced utilizing phosphoramidite chemistry, i.e. by oligomerization of compounds of type (Ia).

The oligomerization may be carried out on a solid support or in solution. Preferably, oligomerization is carried out on a solid support. In fact, oligomerization in solution involves steps of purification by chromatography, steps that are not economically viable, especially for the small quantities required in diagnostic applications.

Another object of the present invention described above is a solid support grafted with an oligomer of a compound (Ia) or of a compound (Ib) and corresponding to the following formula (XVI)$_k$:

(Ic)-(I')$_k$ (XVI)$_k$ in which:
k represents an integer between 1 and 11,
(Ic) has the same meaning as above,
(I') represents (I'a) or (I'b), with:

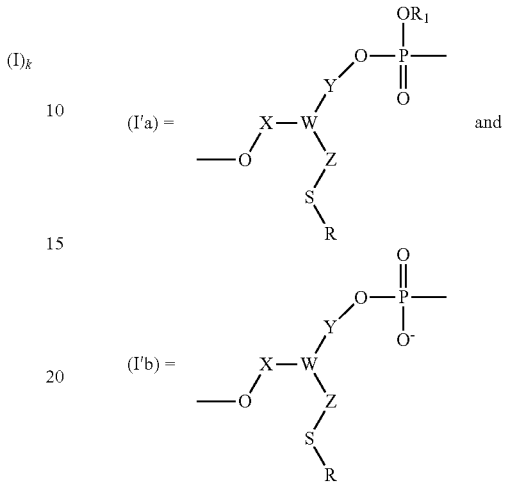

The oligomer on a solid support ☐ formed from a compound (Ic) and from compounds of formula (Ia) corresponds to the following formula (XIV)$_k$:

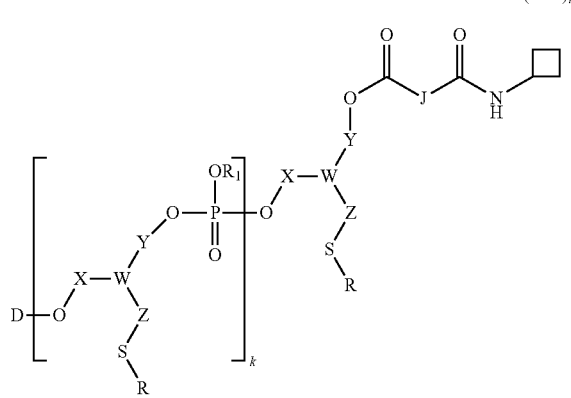

in which ☐, D, X, Y, W, Z, J, R and R$_1$ have the same definition as above and R may in addition represent H; k is an integer between 1 and 11.

The oligomer on a solid support formed from a compound (Ic) and from compounds of formula (Ib) corresponds to the following formula (XV)$_k$:

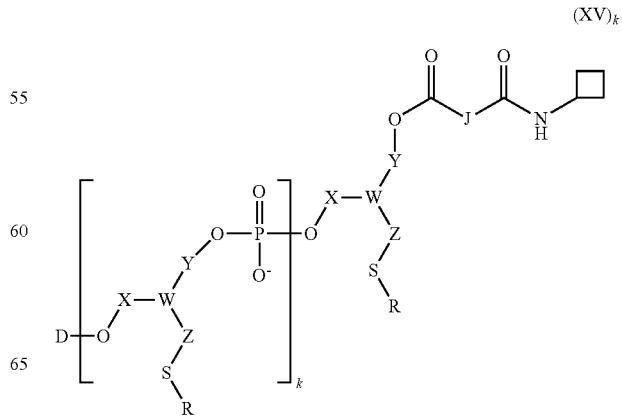

in which ☐, D, X, Y, W, Z, J and R have the same definition as above and R may in addition represent H; k is an integer between 1 and 11.

In the case when the oligomer is formed on a solid support starting from a compound (Ic) and from compounds (Ib), the compound obtained $(XV)_k$ corresponds to the same formula as compound $(XIV)_k$ but in which $R_1$ is a hydrogen atom after oxidation of the H-phosphonate diester bonds.

At the end of the oligomerization reaction, deprotection of the thiol functions by conventional methods may be envisaged and then R represents H.

Modified Oligonucleotides

Another subject of the present invention relates to a modified oligonucleotide, comprising at least one nucleotide, preferably at least two nucleotides and at least one thiol compound (I) as previously described.

In the present application, the term oligonucleotide denotes a chain comprising between 2 and 100 nucleotides.

The thiol compound according to the invention is grafted in position 3', in the chain, or in position 5' of an oligonucleotide.

The preparation process for said modified oligonucleotide comprises at least:
- a step of grafting a compound (I) on an oligonucleotide to give a 5'-thiol oligonucleotide, or
- a step of grafting a nucleotide on an oligomer of a compound (I) to give a 3'-thiol oligonucleotide.

According to an embodiment of the invention, the grafted oligonucleotide corresponds to the following formula (XIIa):

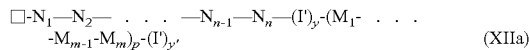
(XIIa)

in which, $N_1, \ldots N_n$ represent, independently of one another, a nucleotide, $M_1, \ldots M_m$ represent, independently of one another, a nucleotide, (I') represents a compound of formula (I'a) or (I' b), n is an integer comprised between 1 and 100, m is an integer comprised between 1 and 100, y is an integer comprised between 1 and 12, p represents 0 or 1, y' is an integer comprised between 0 and 12 if p has the value 1, and y' is equal to 0 if p has the value 0, ☐ represents a solid support.

The modified oligonucleotide (XIIa) has one or more thiol compounds in position 5' of an oligonucleotide N or in the nucleotide chain. Said compound is obtained by grafting a compound (I) followed by elongation of the oligomer obtained from (I) in position 5' of an oligonucleotide. Then, in the case when p=1, elongation of the nucleotide chain continues. Then, in the same way, grafting of one or more additional compounds (I) in position 5' of the oligonucleotide M may be envisaged.

Figure 3:
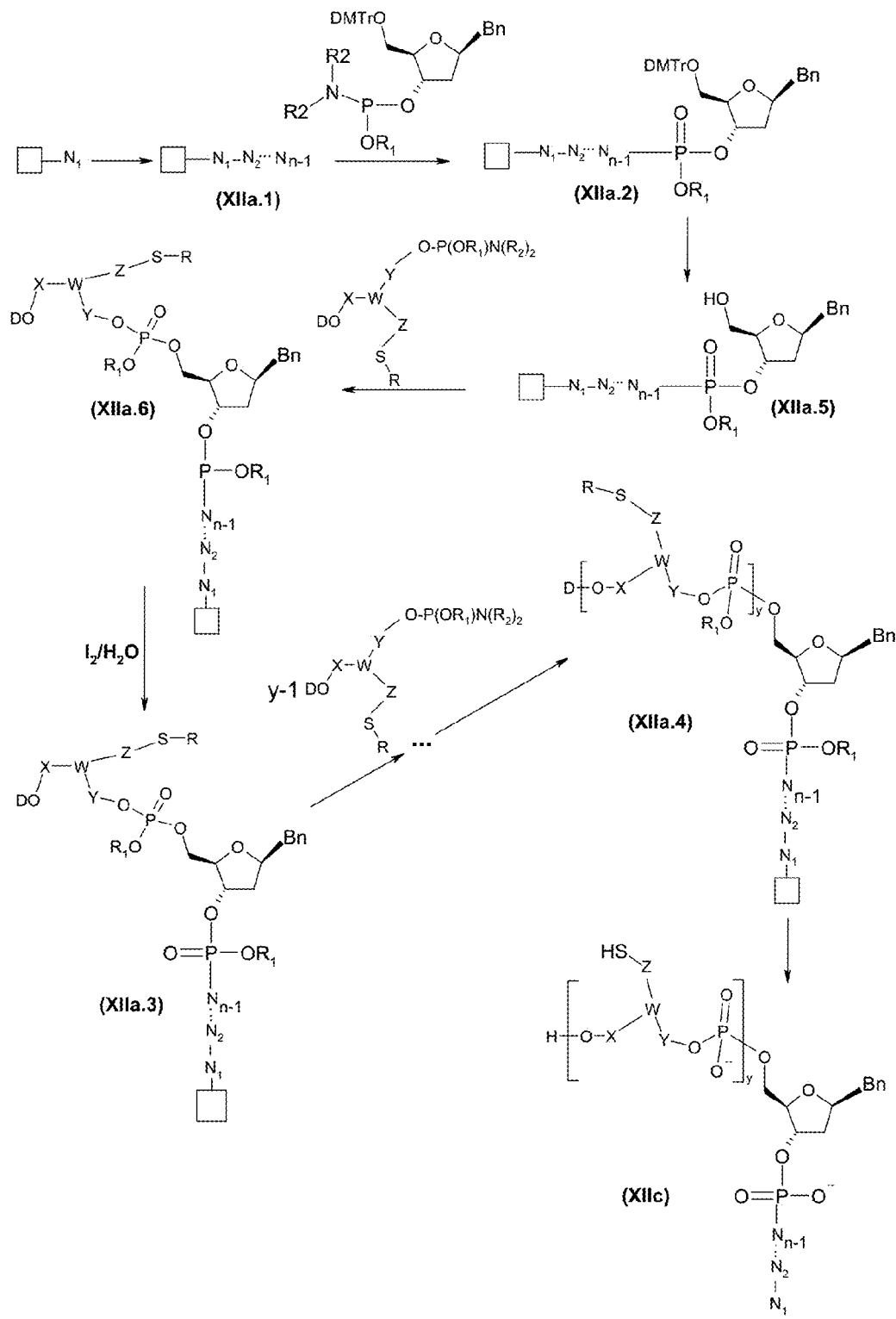
FIG. 3 shows a diagram describing a method of synthesis of an oligonucleotide compound (XIIc) grafted with an oligomer of (I) at its 5' end.

A diagram for obtaining compound (XIIa) is described in FIG. 3, in which the thiol compounds are of type (Ia) and p is equal to 0. The first three steps in the preparation of compound (XIIa) allow synthesis of an oligonucleotide. The oligonucleotide is synthesized on a solid support by a conventional method well known to a person skilled in the art. In the first step, a first nucleotide is grafted on a solid support, then the other nucleotides are grafted by synthesis methods well known to a person skilled in the art. The following compound is obtained:

(XIIa.1)

Then another nucleotide is grafted by an identical method, leading to the compound of formula (XIIa.2).

In the next step, a thiol compound according to the invention of type (Ia), is grafted in position 5' of the oligonucleotide (XIIa.2), leading to compound (XIIa.3):

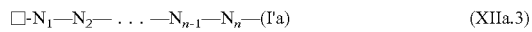
(XIIa.3)

In this step, grafting is carried out conventionally by reaction of the phosphoramidite function of compound (Ia) with the alcohol function in position 5' of the terminal nucleotide of compound (XIIa.2).

In the diagram in FIG. 3, a synthesis example is described with the oligomerization of the thiol compound of type (Ia); a similar synthesis method is used for the synthesis of oligonucleotides modified with thiol compounds of type (Ib).

Then, the oligomerization as described previously, in particular in FIGS. 2A and 2B, takes place starting from compound (XIIa.3) above, by reaction with one or more compounds (Ia) or (Ib), leading to compound (XIIa.4) of formula:

or as a structural formula (In the case when p=0):

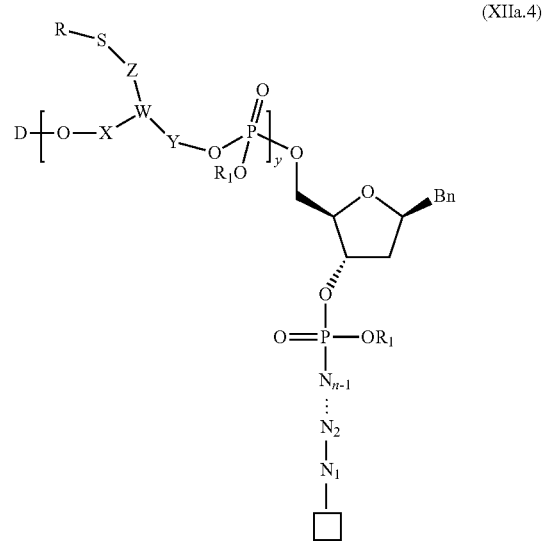
(XIIa.4)

in which,

☐, D, R, X, Y, W, Z, $R_1$ have the same definition as for compound (I) and $R_1$ may in addition represent H, n, y and $N_1, N_2, \ldots N_{n-1}$ have the same definition as for compound (XIIa), Bn represents a base used conventionally in a nucleotide chain.

In the case when elongation of the oligomer is carried out with compounds of type (Ib), the modified oligonucleotide has a structure similar to that of the modified oligonucleotide (XIIa.4) but in which $R_1$ represents H.

Subsequent grafting of nucleotide compounds $M_1$, $M_2, \ldots M_m$ is then possible, leading to the product (XIIa) with p=1. In these cases, elongation also takes place on a solid support.

This grafting step is carried out conventionally by methods known to a person skilled in the art.

According to another embodiment of the invention, the grafted oligonucleotide corresponds to the following formula (XIIIa):

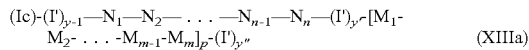  (XIIIa)

in which, $N_1, \ldots N_n$ represent, independently of one another, a nucleotide, $M_1, \ldots M_m$ represent, independently of one another, a nucleotide, (I') represents a compound of formula (I'a) or (I'b), n is an integer comprised between 1 and 100,
m is an integer comprised between 1 and 100,
y is an integer comprised between 1 and 12,
y' is an integer comprised between 0 and 12,
p has the value 0 or 1 if y' is different from 0, and if y' has the value 0 then p has the value 0,
y" is an integer comprised between 0 and 12 if p has the value 1, and if p has the value 0 then y" has the value 0.

Figure 4:
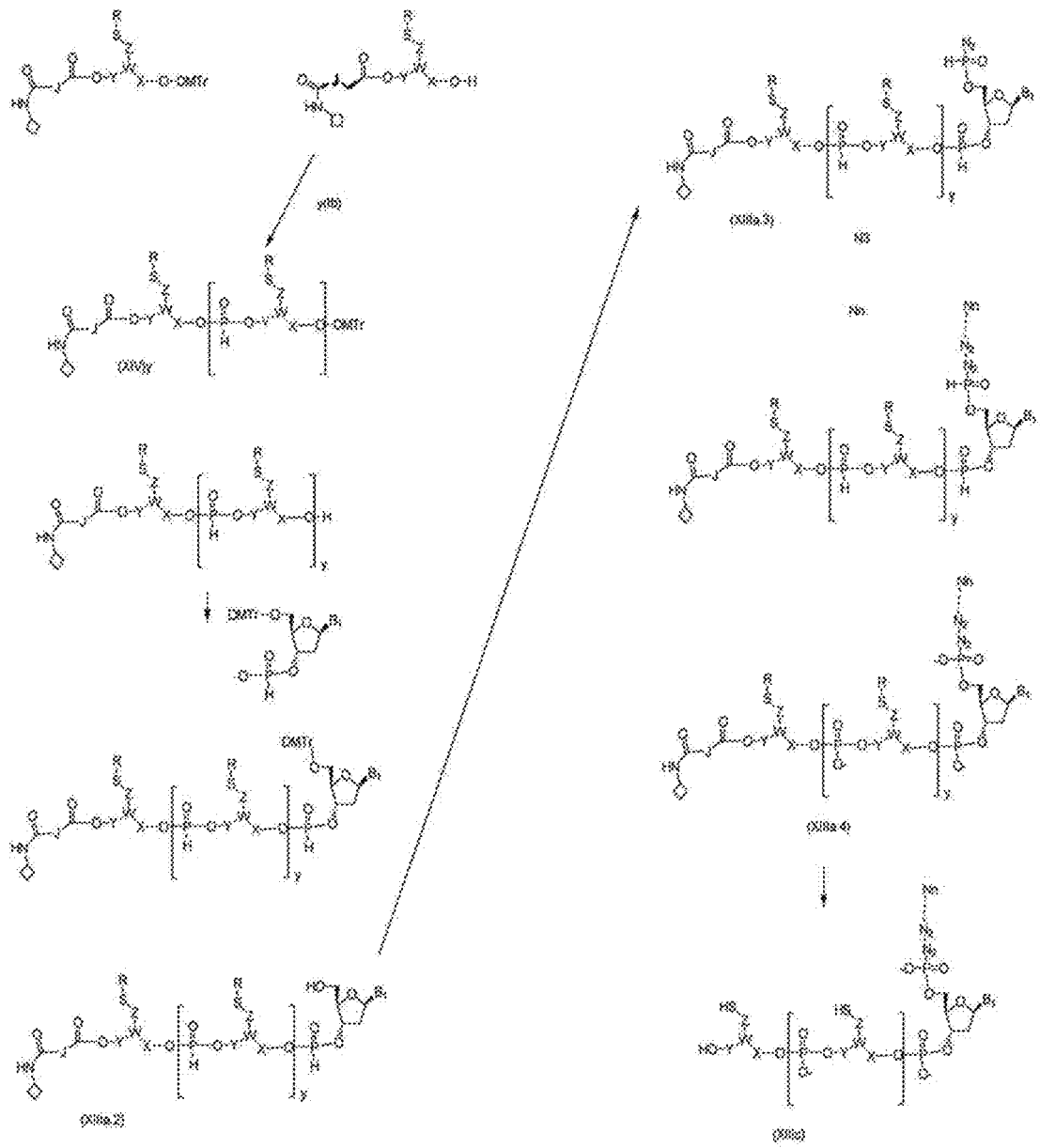
FIG. 4 shows a diagram presenting a method of synthesis of an oligonucleotide compound (XIIIc) grafted with an oligomer of (I) at its 3' end.

A diagram representing a synthesis method of compound (XIIIc) is described in FIG. 4 using an oligomer formed from a compound of type (Ic) where J is an ethyl group, and compounds of type (Ib).

Synthesis of the compound of formula (XIIIc) comprises a first step consisting of the oligomerization of the thiol compound according to the invention of formula (I), the method for which is described above, leading to the compound of formula (XIIIa.1):

  (XIIIa.1)

in which, (Ic) has the same definition as before,
(I') represents a group of type (I'a) or (I"b), where

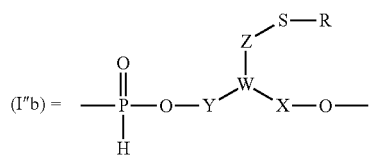

or as a structural formula in the case when (I') represents (I"b):

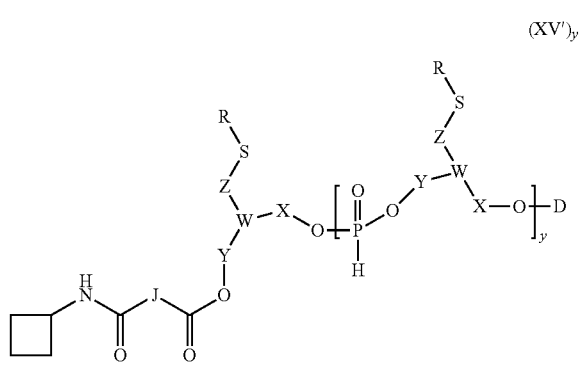  (XV')$_y$

In a second step, a first nucleotide $N_1$ is grafted on the oligomer of formula (XIIIa.1), leading to the compound of the following formula (XIIIa.2):

  (XIIIa.2)

This grafting step is carried out by reaction between the deprotected alcohol function at the end of the oligomer chain of compound (XIIIa.1) and the phosphoramidite or H-phosphonate function of the first nucleotide $N_1$.

The modified oligonucleotide is then synthesized by any method known to a person skilled in the art, in particular a conventional method well known to a person skilled in the art by reaction between the alcohol function at 5' of the first nucleotide present on the oligomer of the thiol compound and the phosphoramidite or H-phosphonate function in position 3' of a second nucleotide. The synthesis continues by similar successive steps of elongation of the nucleotide chain well known to a person skilled in the art, leading to the compound of formula (XIIIa).

Another subject of the present invention relates to the compounds obtained from the compounds of formula (XIIa) and (XIIIa) above after cleavage of the bond that attaches the modified oligonucleotide to the solid support. Bond cleavage takes place at the level of the ester function.

Thus, according to an embodiment of the invention, the unsupported oligonucleotide has the following structure (XIIb):

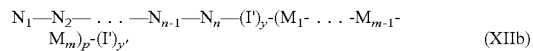  (XIIb)

in which, $N_1, \ldots N_n$ represent, independently of one another, a nucleotide, $M_1, \ldots M_m$ represent, independently of one another, a nucleotide, (I') represents a compound of formula (I' a) or (I' b),
n is an integer comprised between 1 and 100,
m is a number comprised between 1 and 100,
y is an integer comprised between 1 and 12,
p represents 0 or 1,
y' is an integer comprised between 0 and 12 if p has the value 1, and y' is equal to 0 if p has the value 0.

Withdrawal of the support is carried out in two steps, firstly with a non-nucleophilic strong base (piperidine or DBU) in order to eliminate the cyanoethyl groups if present (in the case of phosphoramidites) and secondly by a conventional method known to a person skilled in the art, preferably by treatment of compound (XIIa) with ammonium hydroxide ($NH_4OH$). It is necessary to remove the cyanoethyl groups before deprotection of the thiol groups as they form acrylonitrile during their removal, which reacts strongly with the thiol functions.

According to another embodiment of the invention, the unsupported oligonucleotide has the following structure (XIIIb):

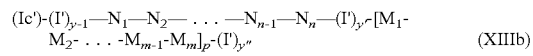  (XIIIb)

in which, $N_1, \ldots N_n$ represent, independently of one another, a nucleotide, $M_1, \ldots M_m$ represent, independently of one another, a nucleotide, (Ic') represents the compound obtained from (Ic) by cleavage of the ester bond with the solid support,
(I') represents a compound of formula (I' a) or (I' b),
n is an integer comprised between 1 and 100,
m is a number comprised between 1 and 100,
y is an integer comprised between 1 and 12,
y' is an integer comprised between 0 and 12,
p has the value 0 or 1 if y' is different from 0, and if y' has the value 0 then p has the value 0, y" is an integer comprised between 0 and 12 if p has the value 1, and if p has the value 0 then y" has the value 0.

Withdrawal of the support is carried out by a conventional method known to a person skilled in the art, preferably by treatment of compound (XIIIa) with ammonium hydroxide (NH$_4$OH).

The present invention further relates to the modified oligonucleotides (XIIc) and (XIIIc) obtained respectively starting from compounds (XIIa) and (XIIIa) by deprotection of the thiol function and cleavage of the bond attaching the compound to the solid support (FIGS. 3 and 4 respectively).

In the case when the oligonucleotide is modified with one or more thiol compounds of type (Ia), after deprotection of the thiol function and of the phosphoramidite function of compound (XIIa) by a treatment known to a person skilled in the art, the compound of formula (XIIc) is obtained:

$$N_1-N_2-\ldots-N_{n-1}-N_n-(I'')_y-(M_1-\ldots-M_{m-1}-M_m)_p-(I'')_{y'} \quad\quad (XIIc)$$

in which, $N_1, \ldots N_n$ represent, independently of one another, a nucleotide, $M_1, \ldots M$ represent, independently of one another, a nucleotide, $$(I'') = \begin{array}{c} HS_{\diagdown Z} \\ \diagup O-X \diagdown W \diagup Y-O \diagdown P \diagup \\ \quad\quad\quad\quad\quad\quad\quad\quad O^- \end{array} \begin{array}{c} O \\ \| \\ \end{array}$$

n is an integer comprised between 1 and 100,
m is a number comprised between 1 and 100,
y is an integer comprised between 1 and 12,
p represents 0 or 1,
y' is an integer comprised between 0 and 12 if p has the value 1, and y' is equal to 0 if p has the value 0,
or as a structural formula in the case when p=0:

(XIIc)

in which,

X, Y, W, Z have the same definition as for compound (I),
$N_1, \ldots N_n$, n, y have the same definition as for compound (XIIa),
Bn represents a base used conventionally in a nucleotide chain.

In the case when the oligonucleotide is modified with one or more thiol compounds of type (Ib), after deprotection of the thiol function of compound (XIIIa) by a treatment known to a person skilled in the art, the compound of formula (XIIIc) is obtained:

$$(Ic')-(I')_{y-1}-N_1-N_2-\ldots-N_{n-1}-N_n-(I'')_y-[M_1-M_2-\ldots-M_{m-1}-M_m]_p-(I'')_{y''} \quad\quad (XIIIc)$$

in which, $N_1, \ldots N_n$ represent, independently of one another, a nucleotide, $M_1, \ldots M_m$ represent, independently of one another, a nucleotide, (Ic') represents the compound obtained from (Ic) by cleavage of the ester bond with the solid support □, $$(I'') = \begin{array}{c} HS_{\diagdown Z} \\ \diagup O-X \diagdown W \diagup Y-O \diagdown P \diagup \\ \quad\quad\quad\quad\quad\quad\quad\quad O^- \end{array} \begin{array}{c} O \\ \| \\ \end{array}$$

n is an integer comprised between 1 and 100,
m is a number comprised between 1 and 100,
y is an integer comprised between 1 and 12, y' is an integer comprised between 0 and 12,
p has the value 0 or 1 if y' is different from 0, and if y' has the value 0 then p has the value 0,
y" is an integer comprised between 0 and 12 if p has the value 1, and if p has the value 0 then y" has the value 0.
or as a structural formula in the case when y'=p=0:

(XIIc)

in which,

X, Y, W, Z have the same definition as for compound (I),
$N_2, \ldots N_n$, n and y have the same definition as for compound (XIIa),
Bn corresponds to a base used conventionally in a nucleotide chain.

During synthesis of the oligonucleotide, the thiol function is preferably protected. In fact, the thiol function may react with the incoming phosphoramidite function.

According to an embodiment, the step of deprotection of the thiol functions and removal of the solid support is carried out in a single step of treatment of the modified oligonucleotide (XIIa) or (XIIIa).

According to an embodiment, the removal of the solid support is carried out in a first step, and the deprotection of the thiol functions is carried out in a second step.

The final oligonucleotide (XIIc) (respectively the final oligonucleotide (XIIIc)) is obtained independently of the starting thiol compound, whether starting from compound (Ia) or from compound (Ib). In fact, regardless of whether monomer (Ia) or (Ib) is used, the thiol monomer unit resulting from the oligomerization reaction corresponds to compound (I") described above.

The grafted supports of formulae $(XVI)_k$ according to the invention allow initiation of oligonucleotide synthesis. Industrial or semi-industrial preparation of the solid supports grafted with sequences of oligomers that will be used as polythiol sequence in position 3' of an oligonucleotide may in particular be envisaged.

Synthesis Kit

Such a solid support grafted with a first oligomer $(Ic)-(I')_k$ may be advantageously used in a kit for the synthesis of modified oligonucleotides. In such a kit, it may be associated with a carrier having receiving zones such as the wells of a multiwell plate wherein synthesis reactions are carried out by methods such as those known for carrying out oligomerization reactions of nucleotides.

Automated Device

Such a kit can be used in an automated device for the oligonucleotide synthesis.

In this case, such a device comprises at least:
distinct containers containing:
Nucleotides,
Coupling activators and
washing agents,
mechanical means for sampling and distribution of product samples, as well as computer means for the controlled implementation of these mechanical means, and:
at least one container in which is placed a solid support grafted with an oligomer $(XVI)_k$, compounds (I) as described above, and/or at least one container containing a compound (Ia) or a compound (Ib).

Such an automation also comprises mechanical means for taking samples in the various containers and distribution means of these samples in the container comprising the solid support. Such means may consist in a set of fluid flow pipes and valves, optionally arranged in microfluidic channels, or articulated arms equipped with pipette sampling. The automatic device also comprises computer means (software) allowing the controlled implementation of these mechanical means, allowing the implementation of sequenced reactions.

Surface Functionalization

The modified oligonucleotides according to the invention may be deposited on a substrate in order to functionalize the surface of this substrate. The substrate may be metallic or made of polymer.

According to an embodiment, the substrate is metallic, for example of copper or titanium, and is partially covered or over its entire surface of a film of gold or platinum, preferably of gold.

In another embodiment, the polymer substrate, for example in polystyrene, is grafted with alkenyl or alkynyl or bromoacetamides or iodoacetamides functions.

According to an embodiment, the polymer substrate is a conductive polymer.

According to an embodiment, the alkenyl or alkynyl functions are activated by a carbonyl function in alpha position, preferably the alkenyl or alkynyl functions are chosen from maleimide, acrylamide, iodoacetamido or bromoacetamido, 2-propynamide or N-alkyl-2-propynamide groups.

For example, the substrate may comprise receiving zones covered with a film of gold or platinum or covered with alkenyl or alkynyl functions, such as acrylamide or maleimide functions on which the modified oligonucleotide is deposited.

Figure 13A:
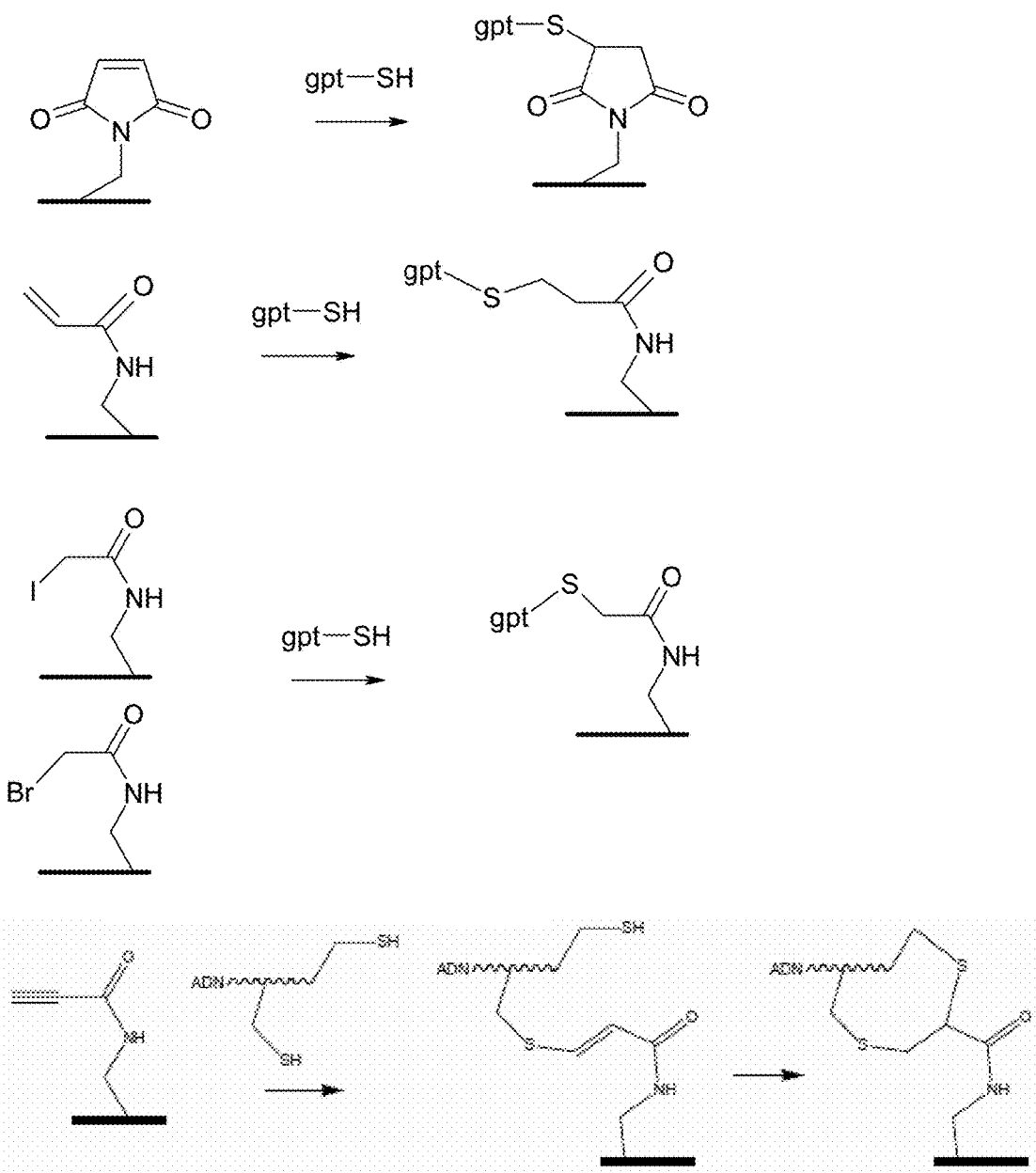
FIG. 13a shows the reactions between the modified oligonucleotide according to the invention and the surface grafted with activated alkenyl or alkynyl groups.

As illustrated in FIG. 13a, wherein the compound gpt-SH represents the modified oligonucleotide (XIIc) or the modified oligonucleotide (XIIIc) according to the invention, the thiol function reacts with the carbon-carbon double bond or triple bond carbon-carbon activated by a carbonyl function in alpha position. From top to bottom of FIG. 13a, the first functionalization reaction corresponds to a maleimide grafted surface, the second reaction corresponds to an acrylamide grafted surface, the third reaction corresponds to a iodoacetamido or bromoacetamido grafted surface and the fourth reaction corresponds to a 2-propynamide grafted surface performed in the case of an oligonucleotide (XIIc) or (XIIIc) modified by two thiol compounds according to the invention.

In the case of FIG. 13b, the surface is grafted with alkenyl groups (first reaction) and alkynyl groups (2nd reaction) not activated. The reaction between the thiol function of the modified oligonucleotide (XIIc) or (XIIIc) is performed using an activation by light ($\lambda$=265 nm). The first functionalization reaction is carried out using a oligonucleotide modified monothiol schematically represented by gpt-SH and the second reaction is carried out using a oligonucleotide modified dithiol.

In case the support is grafted with alkynyl functions, the surface functionalization by a oligonucleotide modified polythiol is very interesting because it leads to a cyclic structure thanks to two successive reactions between a first thiol function and the -yne function in a first step and between a second thiol function and the resulting _ene function in a second step (FIGS. 13a and 13b).

According to a preferred embodiment, the substrate is grafted with maleimide or acrylamide groups.

Thus, the invention allows for example to functionalise a gold surface by creating gold-sulphur bond(s) between the substrate surface and the modified oligonucleotide or to functionalize a grafted surface with maleimide or acrylamide functions by creating thioether bond(s).

The attachment of modified oligonucleotides to the surface of the substrate occurs by contact of the surface to be treated with a solution comprising the modified oligonucleotide, such as those represented by formulae (XIIc) and (XIIIc). Generally, one or more subsequent washing and drying steps are provided. In general, the modified oligonucleotide solution is at a concentration comprised between 0.10 µM and 500 µM, preferably between 0.50 µM and 100 µM for the gold surface and between 50 and 200 nM, preferably between 75 nM and 150 nM for the maleimide or acrylamide, followed by washing to remove the unreacted products.

The presence of several sulfur atoms on the oligonucleotide allow to create several gold-sulfur bonds, or several thioether bonds, which can stabilize the oligonucleotide on the surface.

According to an embodiment, the substrate is non-planar, for example in the form of microparticles or nanoparticles. The modified oligonucleotides according to the invention may then be grafted on these microparticles or nanoparticles. Preferably, these particles are magnetic. In fact, these magnetic particles may then easily be brought to the surface of an electrode or to the bottom of the wells of a microplate, for the purpose of a test for detecting by applying a magnet.

Fixation to Markers or Ligands

The oligomers of the present invention may also be used in order to bond by one or more points of attachment markers or ligands to molecules or polymers. The markers or ligands can be for example, enzymatic, chromogenic, fluorogenic, radioactive, or chemiluminescent markers, metals, metal ions, hormones, proteins, peptides, saccharides, oligosaccharides, nucleolytic or proteolytic agents, binding agents, such as a biotin, an antigen, a hapten, an antibody or a receptor. The markers or ligands may be all compounds of biologic interest which may influence the transport of oligonucleotides through biological membranes and/or may modify the solubility of oligonucleotides.

Test Kits

Another subject of the invention consists of a test and/or diagnostic kit comprising at least one support comprising at least one receiving zone, on which at least one modified oligonucleotide according to the invention is placed.

Thus, the test kit may be used for screening biologically active molecules or for diagnostic or sequencing tests. It may be envisaged that the diagnostic kit comprises several separate receiving zones, on which a solid support grafted with identical or different oligonucleotides is deposited. For example, solid supports grafted with identical or different oligonucleotides may be placed on separate receiving zones of a substrate covered with a gold film or of a substrate grafted with functions comprising at least one carbon-carbon double bond or carbon-carbon triple bond or haloacetamide functions, preferably maleimide or acrylamide functions, so as to form a test and/or diagnostic support.

The support may in particular be a gold electrode. The test kit may comprise an electrochemical cell comprising a working electrode, a counter-electrode and a reference electrode. The working electrode may be of gold, the counter-electrode of platinum and the reference electrode of silver. Investigation of the interaction of a modified oligonucleotide with a molecule to be tested may comprise a step of cyclic voltammetry.

Grafting with alkenyl, alkynyl or haloacetamide functions, such as maleimide or acrylamide functions, may for example be used for applications in the field of diagnostics in the microplate format and/or for carrying out tests of the ELOSA type (Enzyme-Linked OligoSorbent Assay). In the course of this type of test, the surface of the wells is grafted with alkenyl, alkynyl or haloacetamide functions, such as maleimide or acrylamide functions. Then the surface is brought into contact with modified oligonucleotides according to the invention. Thus, one or more thioether bonds form owing to the presence of one or more thiol compounds according to the invention on the oligonucleotides. Then the test consists of contacting a test sample with the wells thus functionalized, in particular for measuring the hybridization of the oligonucleotides. Measurement may for example be based on fluorescence by labelling the oligonucleotide chains.

The invention also relates to the use of a compound comprising at least two thiol functions for functionalized surface grafting with an oligonucleotide, in particular surface functionalized with maleimide or acrylamide. According to an embodiment, the compound may comprise three or four thiol functions. The oligonucleotide immobilized on the maleimide or acrylamide surface, via the compound comprising at least two thiol functions, displays very good stability for use in a diagnostic test, such as a test of the ELOSA type, as well as better availability with respect to the targets. When the number of thiol functions in the compound increases, the number of hybridizations on the whole of the support grafted during the detection test increases. Thus, an oligomer having four thiol functions allows an hybridization of the target which is more effective. Indeed, after having reacted with the oligonucleotide, it allows obtaining excellent results in the detection test of ELOSA type.

EXAMPLES

In the examples, by "probe" is meant an oligonucleotide chain comprising at least one thiol compound according to the invention intended to be immobilized on a surface.

By "target" is meant an oligonucleotide chain intended to hybridize with the probe, for example during a diagnostic test.

Synthesis of the compound 1-O-(4,4'-dimethoxytrityl)-2-(6-S-acetylthiohexyloxymethyl)-2-methylpropane-1,3-diol 4

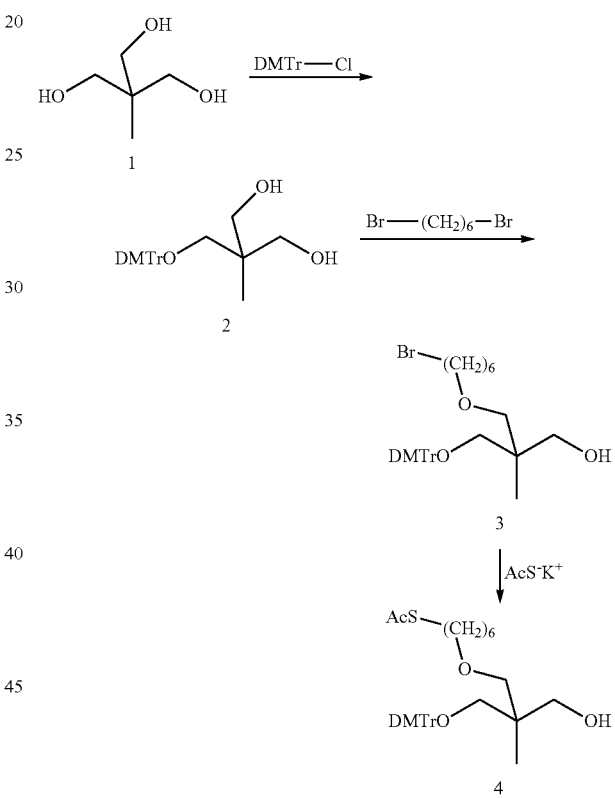

Compound 3 is obtained from compound 1 following the protocol described in Pourceau, G., Meyer, A., Vasseur, J. J., and Morvan, F., *Journal of Organic Chemistry* 74, 2009, 1218-1222.

Crown ether 18-6 (70 mg, 0.26 mmol) is added to a solution of 1-O-(4,4'-dimethoxytrityl)-2-(6-bromohexyloxymethyl)-2-methyl-1,3-propanediol 3 (556 mg, 0.95 mmol) and of potassium thioacetate (162 mg, 1.42 mmol) in anhydrous toluene (10 mL). The mixture is subjected to magnetic stirring for 2 hours at 50° C. After dilution with dichloromethane (150 mL), the mixture is filtered and the organic phase is washed with water (2×50 mL) and then dried over $Na_2SO_4$. After evaporation, the crude reaction product is purified by silica chromatography (0 to 30% of ethyl acetate in cyclohexane), giving the desired product in the form of a colourless oil (413 mg, 75%).

Synthesis of 1-O-(4,4'-dimethoxytrityl)-2-(6-S-acetylthiohexyloxymethyl)-2-methyl-3-O-(2-cyanoethyl-N,N'-diisopropylphosphoramidite)-propane-1,3-diol 5

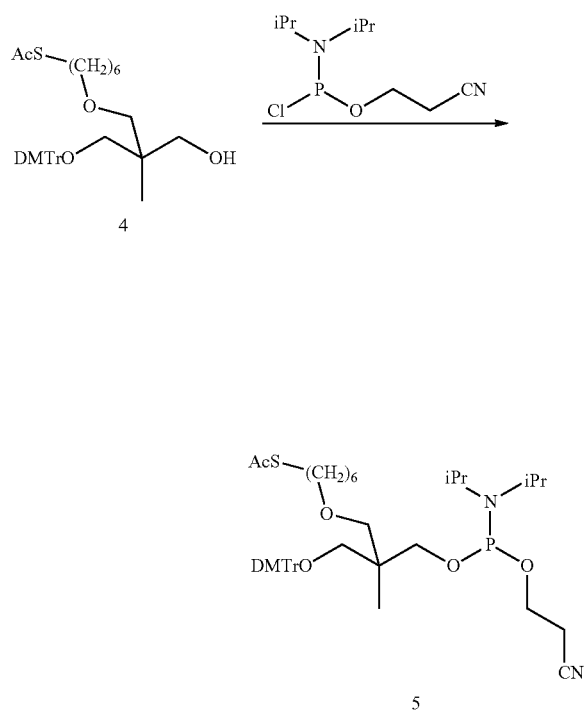

2-Cyanoethyl-N,N'-diisopropylchlorophosphoramidite (190 µL, 0.85 mmol) is added to a solution of 1-O-(4,4'-dimethoxytrityl)-2-(6-S-acetylthiohexyloxymethyl)-2-methylpropane-1,3-diol 4 (413 mg, 0.71 mmol) and diisopropylethylamine (186 µL, 1.06 mmol) in anhydrous dichloromethane (10 mL). The mixture is subjected to magnetic stirring for one hour at ambient temperature. The excess reagent is neutralized by adding 500 µL of water and then the mixture is diluted with dichloromethane (150 mL). The organic phase is washed with a saturated aqueous $NaHCO_3$ solution (100 mL), then dried over $Na_2SO_4$. After evaporation, the crude reaction product is purified by silica chromatography (0 to 30% of ethyl acetate in cyclohexane containing 4% of triethylamine) giving the desired compound 5 in the form of a colourless oil (400 mg, 72%).

Synthesis of the Thiol Solid Support 6

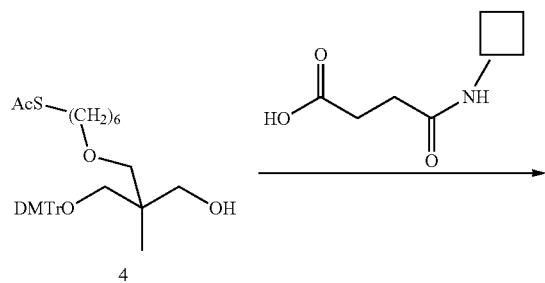

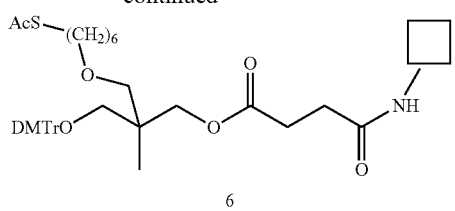

In a ground-glass tube, 1-O-(4,4'-dimethoxytrityl)-2-(6-S-acetylthiohexyloxymethyl)-2-methyl-1,3-propanediol 4 (178 mg, 0.3 mmol) and dimethylaminopyridine (DMAP 36 mg, 0.3 mmol) are coevaporated with 3 mL of anhydrous pyridine. Then succinyl-long chain alkylamine CPG (Controlled Pore Glass) (1 g), anhydrous pyridine (5 mL), anhydrous triethylamine (160 mL, 1.2 mmol) and ethyldimethylaminopropyl carbodiimide (EDC, 280 mg, 2.0 mmol) are added. Then it is rinsed with 1 mL of anhydrous pyridine. The mixture is stirred overnight.

The mixture is filtered and washed with $CH_2Cl_2$ (10 mL) and then dried in a desiccator. The thiol compound on solid support is treated with a solution of acetic anhydride, N-methylimidazole, 2,6-lutidine in THF for 3 h with stirring. The mixture is filtered and washed with $CH_2Cl_2$ (10 mL) and then dried in a desiccator to give the thiol solid support 6 (940 mg) with a functionalization of 29 µmol/g.

Preparation of Modified Oligonucleotides

Three oligonucleotides comprising a ferrocene group in position 5' and an increasing number of thiol compounds of type (Ia) according to the invention (1, 2 and 4 thiol compounds) were synthesized in a DNA synthesizer. The ferrocene group was used in order to visualize the immobilization of the oligonucleotide on the gold surface by cyclic voltammetry. One, two or four thiol groups were introduced onto a solid support of the propanediol type and the DNA sequence SEQ ID NO: 3 was grafted. Finally, an alpha-thymidine phosphoramidite bearing a ferrocene group was introduced in position 5' of the modified oligonucleotide. The deprotection that follows is carried out in two steps. Firstly, the medium is treated with 10% of piperidine in acetonitrile for 10 minutes in order to remove the cyanoethyl group by beta-removal and the resultant acrylonitrile is removed from the medium by washing with acetonitrile. Then treatment with concentrated ammonium hydroxide makes it possible to remove the acyl protective groups on the nucleobases and on the thiol functions and makes it possible to hydrolyse the succinyl linkage (solid support). This protocol makes it possible to avoid Michael addition between the deprotected thiol functions and the acrylonitrile. After evaporation, the unsupported modified oligonucleotide is purified by reversed-phase HPLC chromatography on a C18 column.

Tetrathiol (Oligonucleotide Modified with 4 Thiol Compounds)

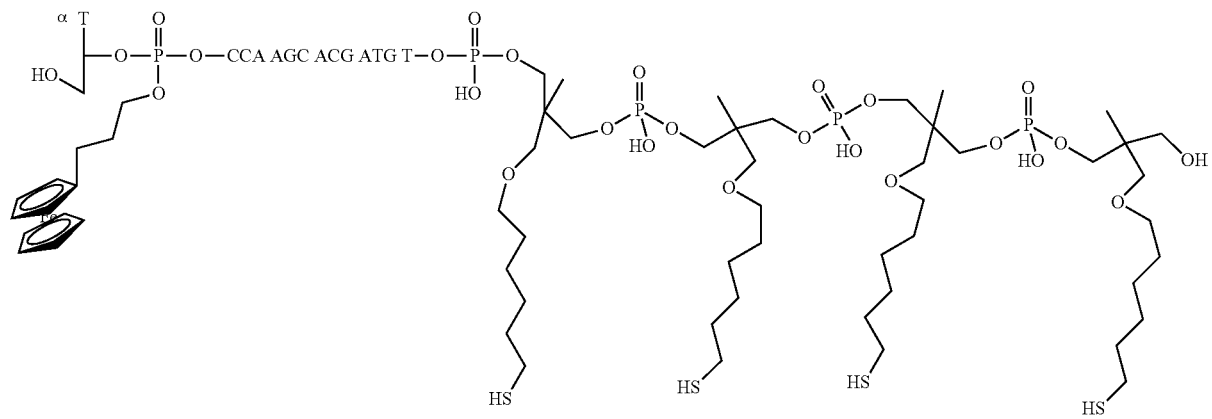

Dithiol (Oligonucleotide Modified with 2 Thiol Compounds)

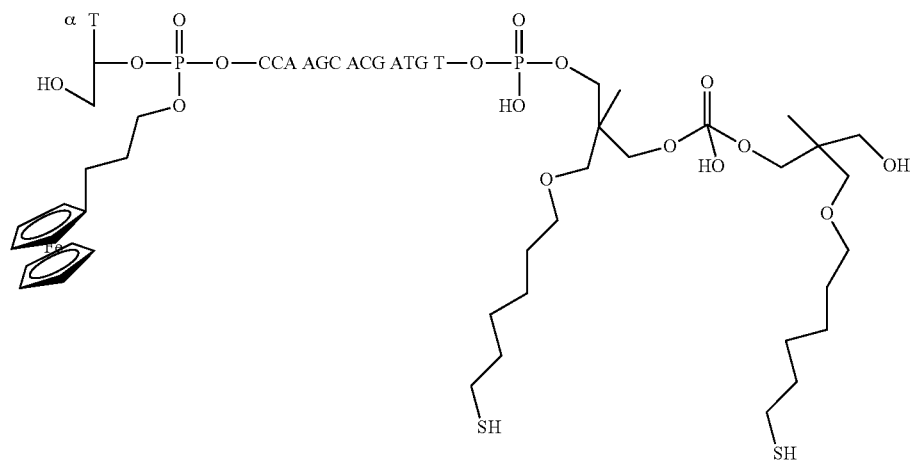

Monothiol (Oligonucleotide Modified with 1 Thiol Compound)

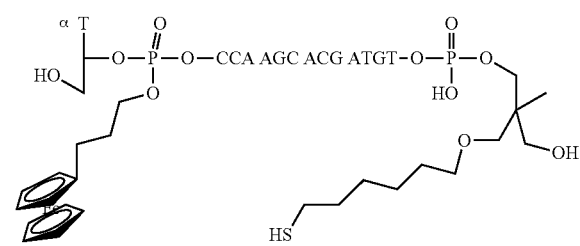

Grafting and Investigation of Stability of the Modified Oligonucleotides (Tetrathiol, Dithiol and Monothiol)

For this study, a VMP3 Biologic multichannel potentiostat (Biologic Science Instruments, Pont de Claix) was used. The results were recorded using the EC-Lab software from Biologic Science Instruments.

The electrochemical cell consists of a gold electrode with surface area of 0.28 cm$^2$, a platinum counter-electrode and an Ag/AgCl reference electrode.

Step 1: Reduction of the Thiol Groups 4 nmol of ODN-thiol (oligonucleotides modified with one or more thiol compounds) is reduced in a solution of Tris(2-carboxyethyl)phosphine hydrochloride (TCEP, HCL, Sigma-Aldrich) (160 mM) i.e. a concentration of 20 mM of TCEP, HCl in the solution, at 20° C., for 2 h under argon.

The ODN is purified by two successive dilutions/centrifugations with a solution of TCEP, HCl 20 mM degassed on amicon YM3000 filters (millipore) for 15 min at 14000 rcf (rcf=Relative Centrifugal Force). After dilution in 450 µL of degassed 100 mM phosphate buffer, the medium is centrifuged again on amicon YM3000 filters, 30 min, 14000 ref.

A grafting solution containing 4 nmol of ODN, 90 mM of sodium phosphate, 2 mM of TCEP, HCl is obtained.

Step 2: Activation of the Gold Electrode

The gold working electrode is cleaned by a first washing in acetone for 10 minutes with ultrasound. Once dried, the surface is immersed in a "piranha" solution (0.7 mL H$_2$SO$_4$, 0.3 mL H$_2$O$_2$) for 1 minute in order to remove any organic residue from the surface.

Finally basic activation of the electrode consists of surface cleaning of the gold by generation of hydrogen at the electrode by hydrolysis of water in 0.5M soda at negative potentials (−1.4V vs Ag/AgCl) for several cycles.

Step 3: Grafting of the Probe

After rinsing, the grafting solution containing the thiol oligonucleotide is brought into contact with the activated gold electrode, for three days under inert atmosphere.

After rinsing, the electrochemical cell is filled with the analysis electrolyte (10 mM dibasic sodium phosphate, 10 mM monobasic potassium phosphate, 250 mM sodium perchlorate, pH 6.5).

The surface is passivated with a 1 mM mercaptopropanol solution for 30 minutes, and after rinsing, the cell is put in the analysis electrolyte for 2 h in order to stabilize the grafted layer.

Step 4: Analysis of the Stability of the Surface Grafted Compounds

The analyses are carried out by cyclic voltammetry (CV) at 50 mV/s, between −0.1V and 0.45V. Studies of the stability of the grafted layer are carried out after stabilization of the electrochemical signal for 2 h by cycling every 30 minutes.

The cell is filled with distilled water degassed at 60° C. or 80° C. for 1 or 5 minutes, and after rinsing, the cell is filled with 1.5 mL of analysis electrolyte phosphate (20 mM) perchlorate (250 mM). After stabilization for 30 minutes, CV is carried out.

The operation is repeated as often as necessary.

Results

Comparison of the degree of grafting of the 3 oligonucleotides modified with thiol compounds (tetrathiol, dithiol and monothiol) was carried out. The degree of grafting was determined by integration of the oxidation peak of the ferrocene. In fact, the electron charge transferred is directly related to the number of ferrocenes present at the surface of the electrode, and therefore to the number of probes grafted on the gold.

The results given below correspond to the mean value of the degrees of grafting of 3 different graftings for each probe.

|  | molecules/cm$^2$ |
| --- | --- |
| monothiol | 5.21E+12 |
| dithiol | 5.81E+12 |
| tetrathiol | 1.40E+12 |

Figure 5:
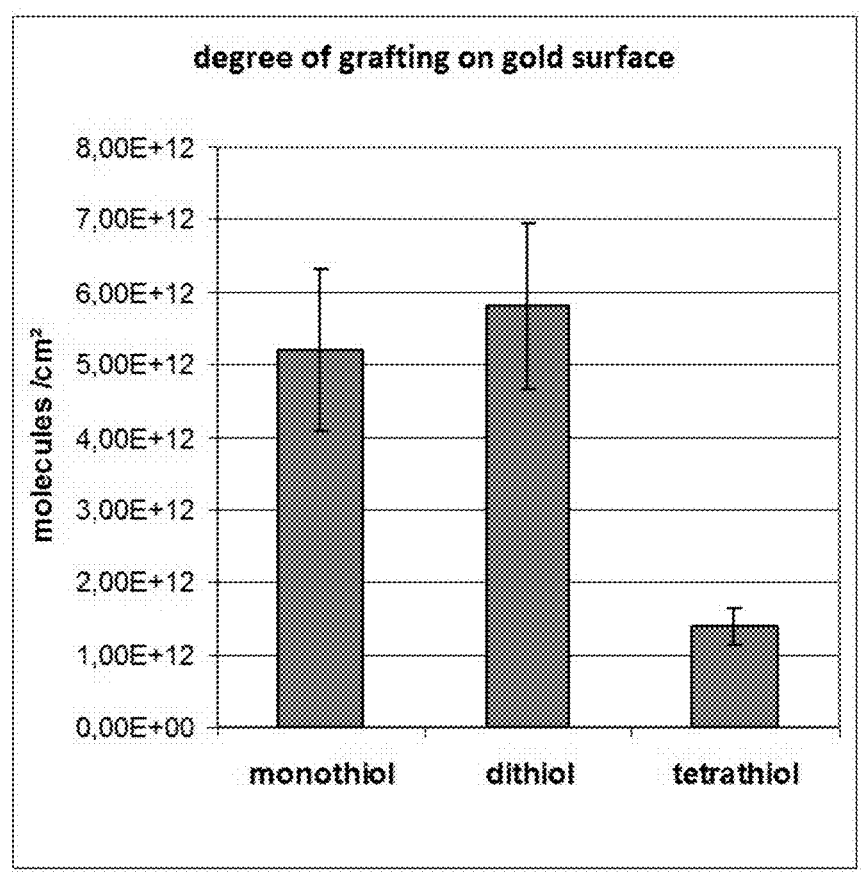
FIG. 5 shows a histogram of the degree of grafting of modified oligonucleotides on a gold surface.

A histogram of the results is shown in FIG. 5.

The degrees of grafting for monothiol and dithiol are fairly comparable, and a lower level of grafting of tetrathiol is observed, probably due to greater hindrance, in keeping with the number of thiol linkages. Despite this difference, the degree of grafting of the tetrathiol is still considerable and it is very reproducible.

A stability test on the 3 oligonucleotides modified with thiol compounds with respect to temperature was carried out in degassed distilled water. The evolution of the electrochemical response was monitored by cyclic voltammetry. The percentage decrease in intensity of oxidation of the ferrocene is calculated relative to the signal obtained after stabilization.

Figure 6:
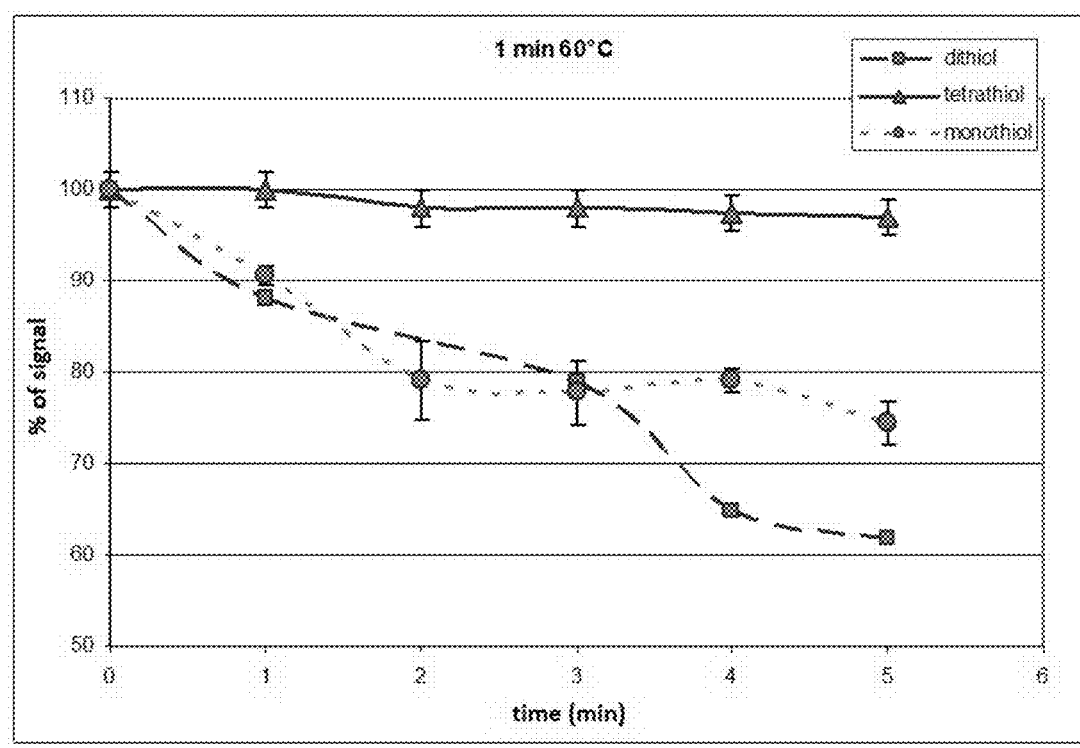
FIG. 6 shows a diagram presenting the stability of grafting of modified oligonucleotides on a gold surface as a function of time at 60° C.
Figure 7:
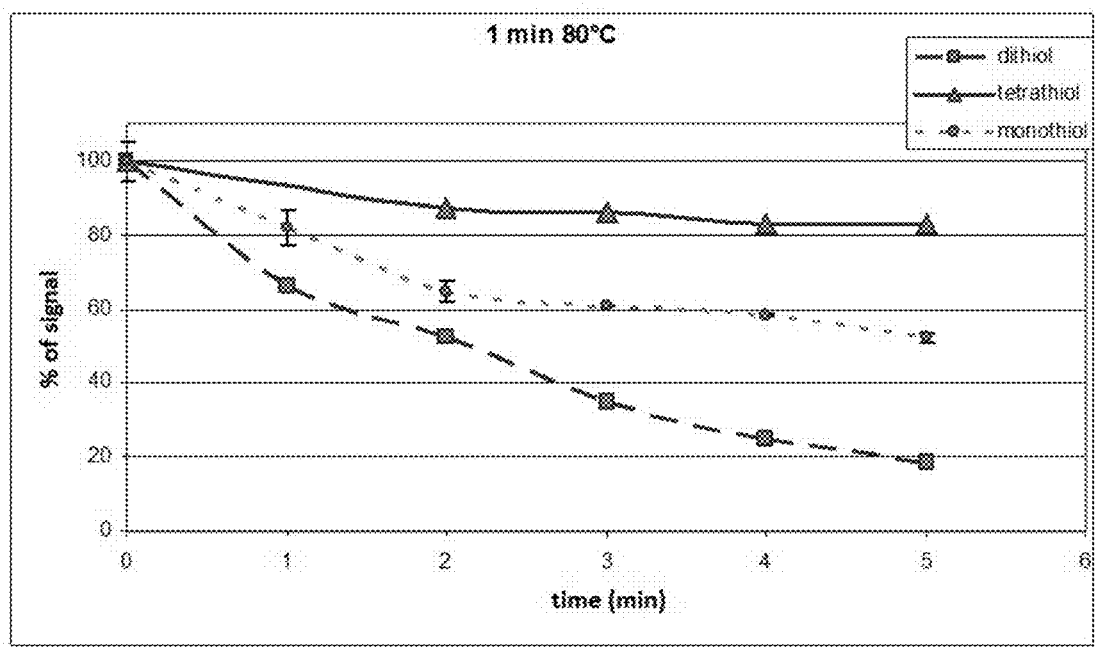
FIG. 7 shows a diagram presenting the stability of grafting of modified oligonucleotides on a gold surface as a function of time at 80° C.

These decreases as a function of time are presented in FIGS. 6 and 7.

The tetrathiol molecule is very stable with respect to successive treatments in water at 60° C. (FIG. 6). In fact, after 5 times one minute of this treatment, 97% of the starting signal remains, in contrast to monothiol (70% of starting signal) and dithiol (62% of starting signal).

At 80° C., the loss of signal is greater (FIG. 7). After five successive treatments of one minute, 83% of the starting signal is again quantifiable for the tetrathiol. Thus, the stability of the tetrathiol is well above that of the monothiol (45% of residual signal) and that of the dithiol (18% of residual signal).

This study shows the notable gain in stability of thiol grafting on gold by using an oligonucleotide modified with 4 thiol compounds (tetrathiol), in comparison with grafting of a monothiol or of a dithiol. The lack of stability of this last-mentioned dithiol may be due to possible competition between grafting on gold and ring closure for reforming the intramolecular disulphide bridge. It therefore appears preferable to maintain a number of four thiols on the grafting linkage to ensure good stability with respect to temperature.

Application: Detection of the Presence of Hepatitis C Virus Target Samples to be Tested 1) Natural Targets: HCV(+) Amplicons Sampling: the plasma samples from blood donors, tested positive for the presence of Hepatite C virus (HCV) at the national scale, are analysed by sequencing.

Amplification of viral RNA: HCV amplicons of 40 lbp are produced in the NS5b viral region, by RT-PCR from the plasma samples described above. The RNA is extracted from 200 µL of human plasma using the High Pure Viral Nucleic Acid kit (Roche) according to the manufacturer's recommendations. The RNA is eluted in 50 µL of sterile water (DNase/RNase free). For the reverse-transcription (AT) step, 11 µL of RNA is denatured at 72° C. for 10 minutes and reverse-transcribed in the presence of 4 µL of 5× First Strand Buffer (Invitrogen), 2 µL of 10× Hexanucleotide Mix (Roche), 2 µL of 10 mM dNTP mix (Invitrogen) and 200 U of SuperScript® II Reverse Transcriptase (Invitrogen). The reverse-transcription conditions are as follows: 10 min at 23° C., 45 min at 37° C., and 10 min at 95° C.

Five microliters of cDNA are then amplified by PCR (polymerase chain reaction) using the primers "Biotinylated HCVsense" (SEQ ID NO: 1 [Btn] Tgg ggA TCC CgT ATG ATA CCC gCT gCT TTg A) and "HCVantisense" (SEQ ID NO: 2 ggC ggA ATT CCT ggT CAT AgC CTC CgT gAA) (see Catherine Tamalet, Philippe Colson, Hervé Tissot-Dupont, Mireille Henry, Christian Tourres, Natacha Tivoli, Danielle Botta, Isabelle Ravaux, Isabelle Poizot-Martin and Nouara Yahi. 2003, *Journal of Medical Virology* 71: 391-398) in 50 µL of reaction mixture: 1×PCR Buffer without MgCl$_2$ (Invitrogen), 0.2 µM of each primer, 1.5 mM MgCl$_2$ (Invitrogen), 0.2 mM dNTP mix (Invitrogen) and 1.3 U Taq Polymerase (Invitrogen). The PCR conditions are as follows: 5 min at 95° C., 40 cycles (denaturation: 40 s, 95° C.; hybridization: 40 s, 56° C.; elongation: 50 s, 72° C.), and a final extension of 10 min at 72° C.

The HCV amplicons obtained are analysed by agarose gel electrophoresis, aliquots are taken and stored at −20° C. before use.

2) Synthetic Targets: Biotinylated Oligonucleotides 15-mer oligonucleotides biotinylated at the 5' end were synthesized. These oligonucleotides are strictly complementary to the HCV probes selected as follows.

Design of the Oligonucleotide Probes for Recognition of HCV Sequences

The NS5b region of HCV was targeted for designing the oligonucleotide probes.

The HCV genome sequences amplified in the NS5b region (bank of 800 samples) were analysed using the clustalW2 alignment software and Mega5 phylogeny software in order to identify the most conserved zones. A highly conserved region permitting specific amplification of all the genomes of viral genotype 1a1b was selected as well as a second region permitting specific amplification of the genomes of viral genotype 3a. Two 15-mer probes were designed complementary of each of those regions. The design of probes 1a1b and 3a is thus used for the synthesis of multi-thiol oligonucleotides.

Evaluation of the Probe/Target Hybridizations by ELOSA (Enzyme-Linked Oligosorbent Assay)

Grafting of any type of thiol probes (alpha-anomer or beta-anomer oligonucleotides, linear or structured (for example stem-loop) probes may be carried out according to this optimized protocol after washing the maleimide-activated microplate wells (Pierce) with WB1 buffer (0.1M $Na_2HPO_4$, 0.15M NaCl, 0.05% Tween 20 (w/v), pH 7.2). Functionalization of the wells is carried out with 100 nM of multi-thiol probes in BB buffer (0.1M $Na_2HPO_4$, 0.15M NaCl, 10 mM EDTA, pH 7.2) for 2 hours at ambient temperature (AT). The wells are then washed three times with WB1 saturated with 10 µg·mL$^{-1}$ cysteine-HCl solution in BB (Pierce) for 1 hour at AT, and washed again three times with WB1.

The hybridization tests may be carried out with the short 15-mer synthetic targets or with real HCV amplicons: long (401 nucleotides) described above. The synthetic targets and the amplicons are diluted in 150 µL of hybridization buffer (HB: 0.9M NaCl, 60 mM $NaH_2PO_4$, 6 mM EDTA, pH 7.4, Denhardt 5×) before being deposited in the wells. An additional denaturation step of 10 min at 95° C. is carried out on the amplicons before transfer to the microwells. Hybridization is carried out overnight at 37° C. The wells are washed with WB2 buffer (0.75M NaCl, 50 mM $NaH_2PO_4$, 5 mM EDTA, pH 7.4, SDS 0.1%) three times for 2 min at AT and once for 30 min at 50° C.

The detection step is carried out after incubation for 30 min at AT of the wells in the presence of 100 µL/well of Streptavidin-Europium diluted in 100 µL of assay buffer ("Assay Buffer", Perkin Elmer). The wells are finally washed six times with WB3 buffer (WB1X, Perkin Elmer), and 200 µL of amplification buffer ("Enhancement Buffer", Perkin Elmer) is added to each well for 5 min at AT. The time-resolved fluorescence is measured on a Victor$_3$™ 1420 multi-labelling detector ("multilabel counter", Perkin Elmer) according to the manufacturer's protocol (excitation at 340 nm and emission at 615 nm).

The ELOSA test is carried out with amplicons specific to the HCV 3a genotype (dilutions of 1/10, 1/100 and 1/1000) and with amplicons specific to the HCV 1a1b genotype (therefore non-specific to the 3a genotype). The control of hybridization is carried out with synthetic targets (15-mer) specific to the 3a genotype (complementary of the probe), tested at 1000 pM and 5 pM and synthetic targets specific to the 1a1b genotype, tested at 1000 pM.

Figure 8:
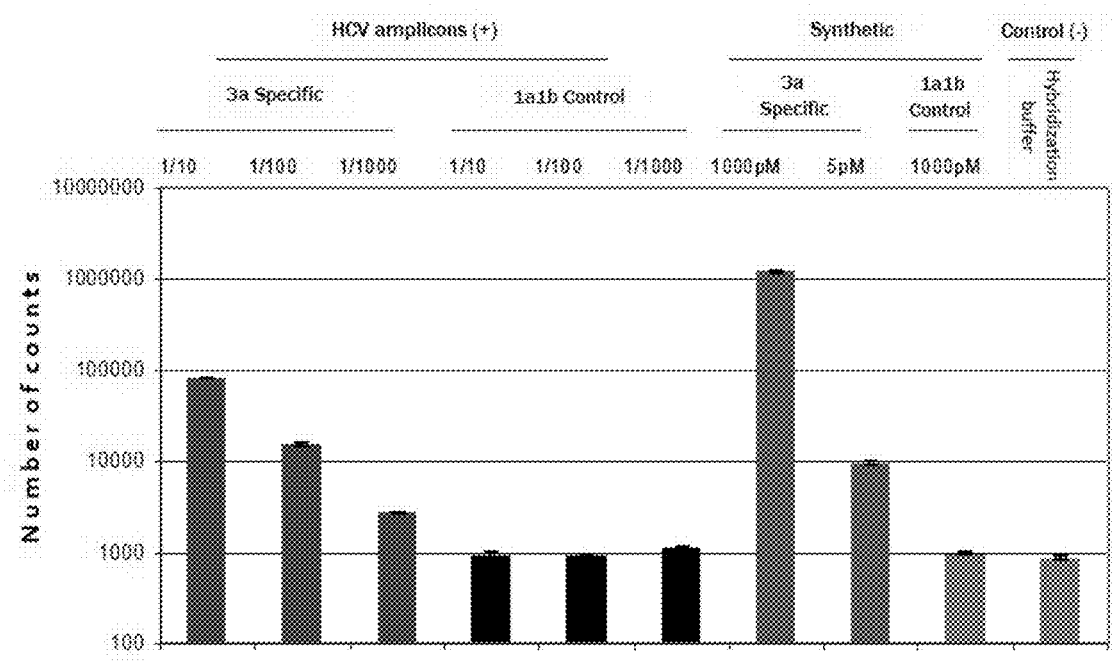
FIG. 8 shows the results of an ELOSA test with fluorescence detection.

The graph of FIG. 8, corresponding to the fluorescence test, illustrates the results of the ELOSA test and quantified the hybridization with the tetrathiol probe corresponding to HCV genotype 3a. Tests "control 1a1b" correspond to the background noise; results "specific 3a" must exceed the background noise for the test makes it possible to quantify hybridization.

Study of the Effect of the Grafting Density

The same ELOSA test is performed by changing the concentration of the probe solution (monothiol, dithiol and tetrathiol) for varying from 1 nM to 100 nM. The ELOSA test is performed with 1a1b and 3a targets with short chains (15-mer) and with medium-chain (105-mer). Tests performed with the probes specific to the 1a1b genotype show a very good hybridization specificity with the 1a1b specific targets and no hybridization with the non-complementary 3a genotype target.

The detection of the hybridization probe/target is performed as above by fluorescence (FIG. 8).

Figure 9:
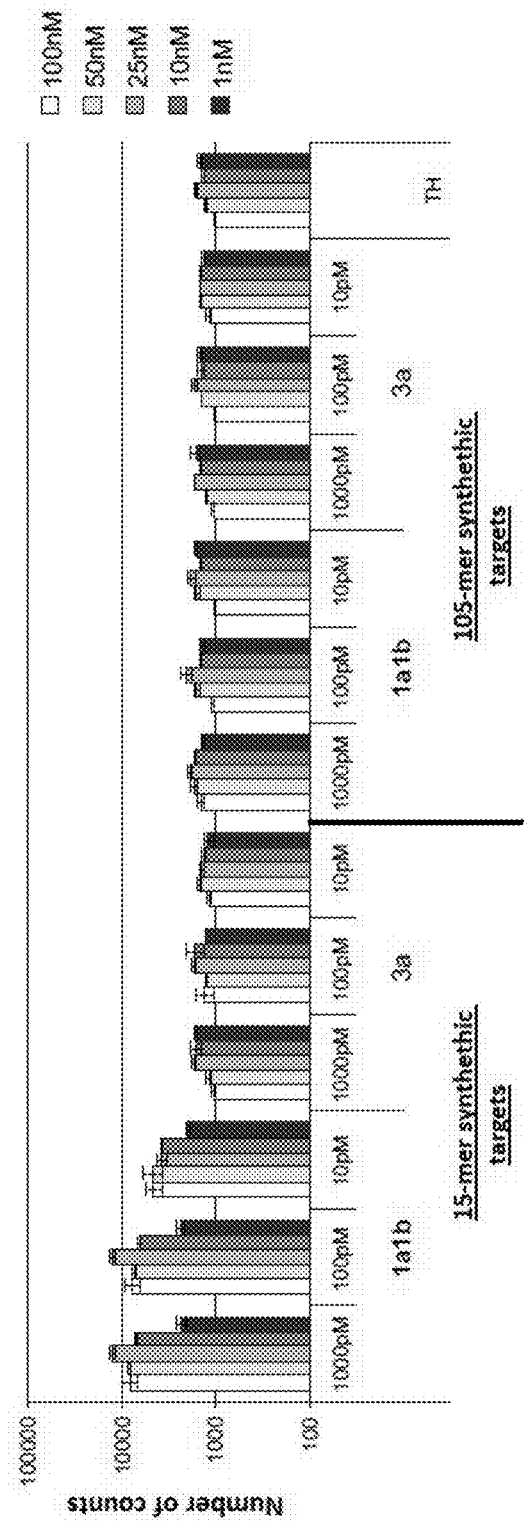
FIG. 9 shows the results of a hydridization test probe/target with a monothiol probe.
Figure 10:
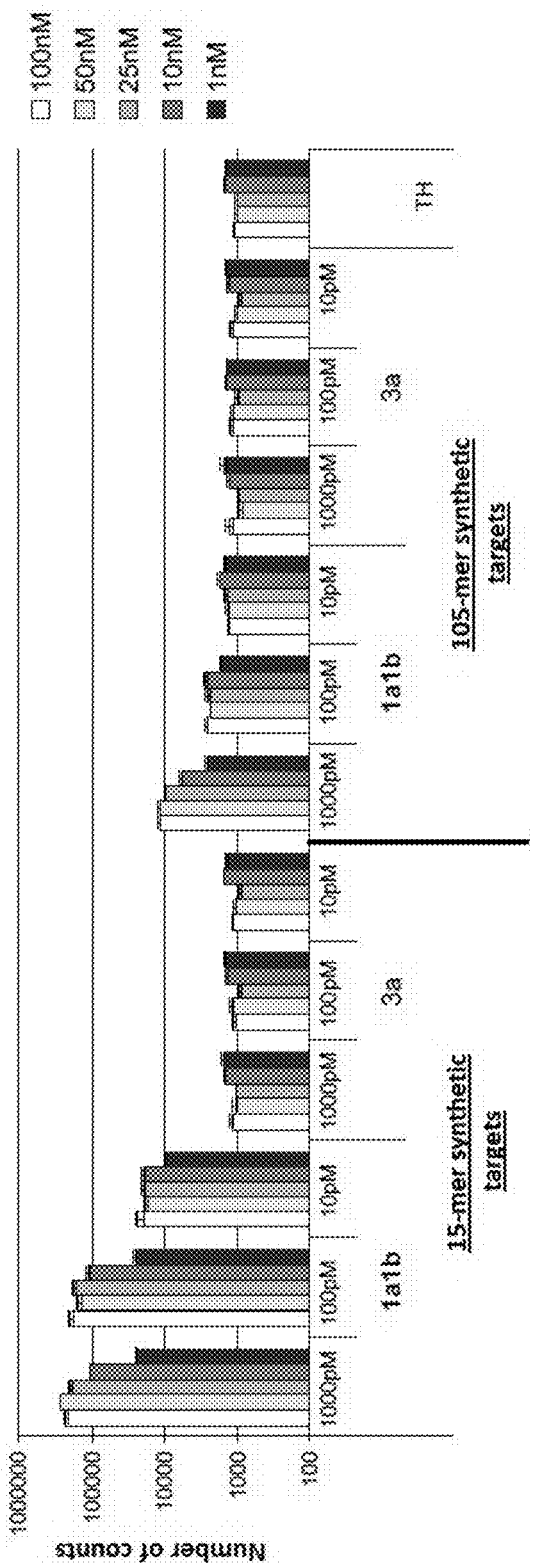
FIG. 10 shows the results of a probe/target hybridization test with a dithiol probe.
Figure 11:
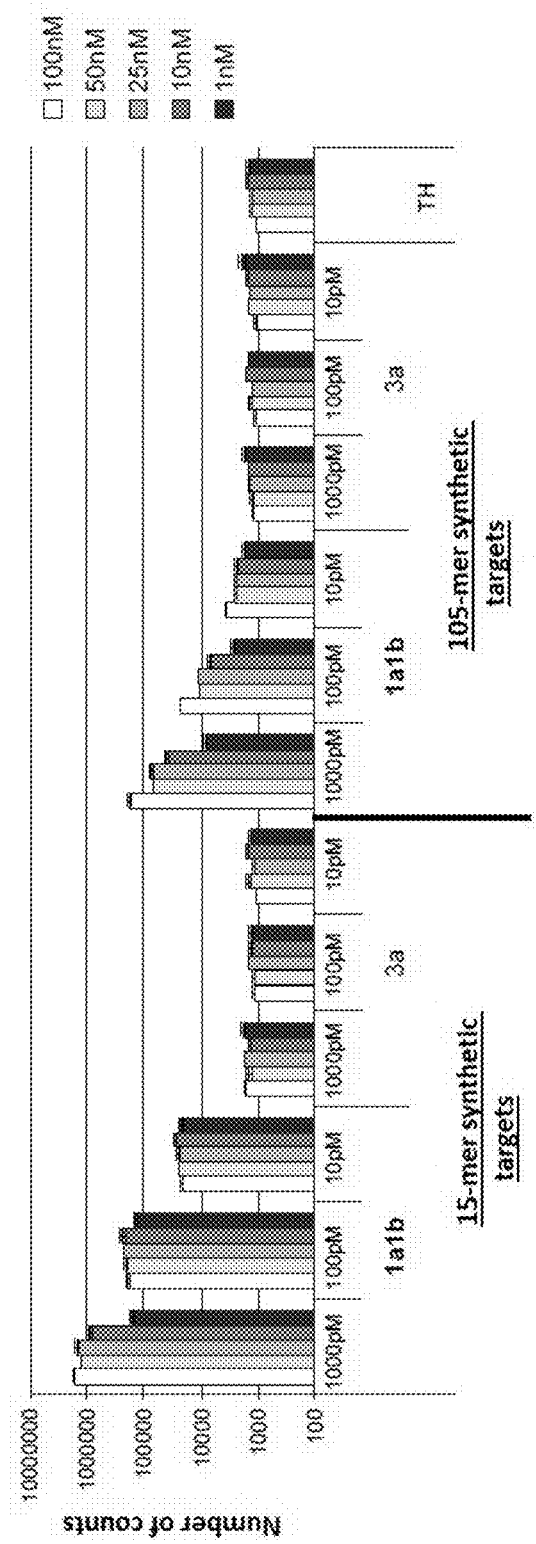
FIG. 11 shows the results of a probe/target hybridization test with a tetrathiol probe.

The results for each type of probes (monothiol, dithiol and tetrathiol) are shown in the graphs of FIGS. 9, 10 and 11. The TH control corresponds to a test performed in the wells but without the presence of the probes. Other probes (comprising 6 and 8 thiols) were also tested and are shown in FIG. 14.

FIG. 9 illustrates the results obtained for the monothiol probe, i.e. comprising a single thiol compound according to the invention. The monothiol probe is not efficient for the detection of 105-mer target, the signal for the 105-mer target is identical to the signal of TH control. In addition, FIG. 9 also shows that the concentration of probe used for grafting between 10 nM and 100 nM had no effect on the efficiency of hybridization, in effect, there is no significant difference between the test performed with 10 nM of probes and the one performed with 100 nM of probes. However, the use of a concentration of 1 nM of probe causes a decrease in the efficiency of hybridization.

FIG. 10 illustrates the results obtained for the dithiol probe, i.e. comprising two thiol compounds according to the invention. The dithiol probe has little effect for the 105-mer target detection, a detection of hybridization is seen for a concentration of 1a1b target of 1000 pM. Furthermore, FIG. 10 shows that the density of grafting slightly affects the detection of the hybridization. Indeed, the fluorescence signal is greater when the concentration of probes goes from 1 nM to 100 nM with little difference between 25 nM and 100 nM.

Figure 14:
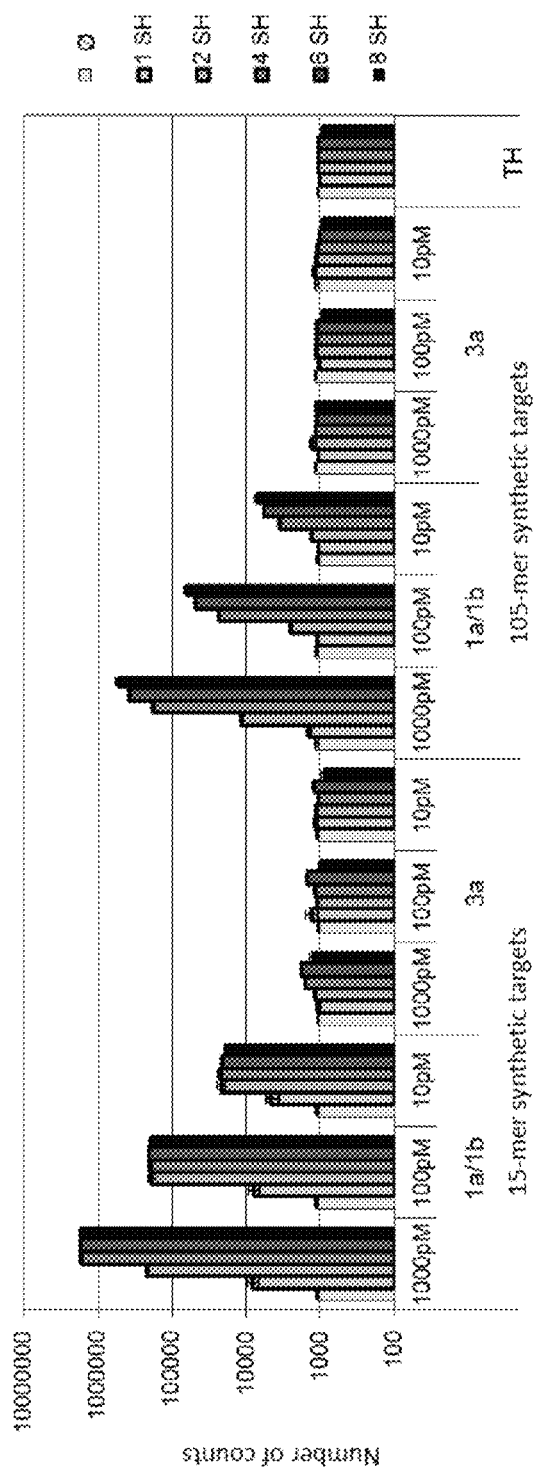
FIG. 14 shows the results of a probe/target hybridization test with probes respectively comprising 1, 2, 4, 6 and 8 thiol compounds according to the invention.

FIG. 14 illustrates the results obtained for the tetrathiol probe, i.e. comprising four thiol compounds according to the invention. The tetrathiol probe is very efficient for detection of 105-mer target, the fluorescence signal is greater than the fluorescence signal of the TH control, particularly for a target concentration of 100 pM and 1000 pM. Furthermore, FIG. 11 shows that the grafting density affects the detection of hybridization for 105-mer. Indeed, for the same concentration of target, for example 1000 pM, the fluorescence signal is greater when the concentration of probes is of 100 nM, as compared with a probe concentration of 1 nM. This effect, also known as "dose dependency", is very pronounced for the detection of 105-mer target.

FIG. 14 shows that the probes comprising 6 or 8 thiols give satisfactory hybridization results. Indeed, the fluorescence signal for those two probes was similar to that of the tetrathiol probe.

Figure 12:
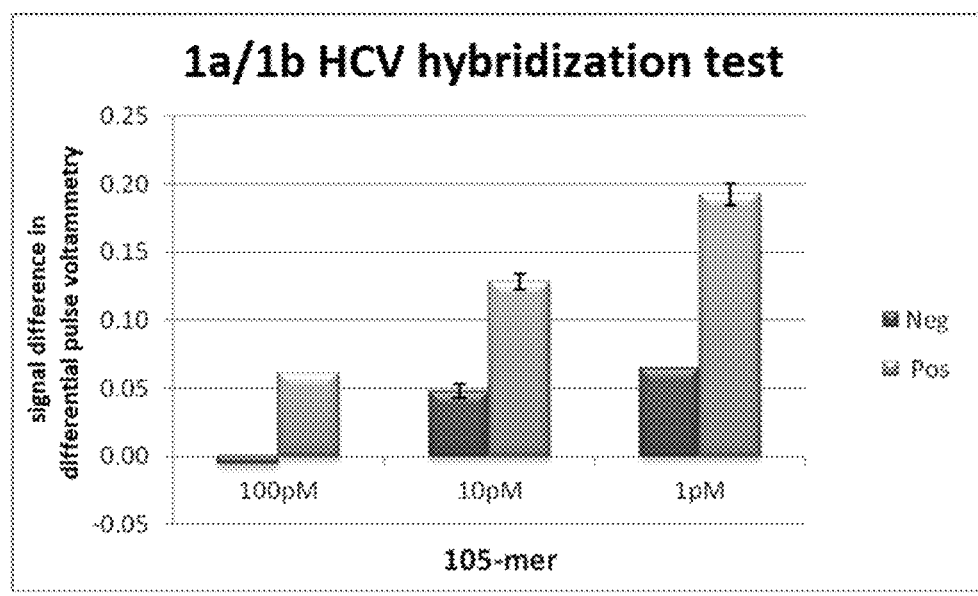
FIG. 12 shows the results of a probe/target hybridization test with a tetrathiol probe grafted on the gold surface.

FIG. 12 illustrates the results of a hybridization test conducted with the sequence for genotype 1a/1b of HCV. The test is conducted at three concentrations in target, 100 pM, 10 pM and 1 pM, with synthetic targets of 105 bases in length. The negative control is conducted with the target 3a non-complementary. The tetrathiol probe 1a/1b is grafted on the working electrode having a gold surface of the electrochemical cell. The hybridization reaction is monitored by differential pulse voltammetry. The values mentioned on the y-axis correspond to the normalized values of the change in current. This test by electrochemistry is sensitive and specific at a concentration of targets of 1 pM. The variation in signal appears to be greater than for the test conducted at 100 pM. At a higher concentration of target, an effect of non-specific adsorption of the targets on the surface of the electrode reduces the efficacy of the recognition reaction. The signal variation of the test conducted at 100 pM appears to be lower than the signal variation observed for the test at 1 pM. This electrochemical method does not allow quantitative monitoring of the hybridization reaction. Nevertheless, it supplies a specific yes/no response with very high sensitivity.

The invention claimed is:

1. A compound corresponding to the following formula (I):

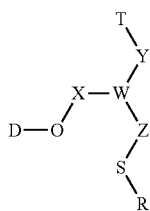

in which:
- T is a group selected from —O—P(OR$_1$)N(R$_2$)$_2$, —O—PH(O)O—, —OC(O)JC(O)NH-☐,
- R$_1$ is selected from 2-cyanoethyl and R'$_1$R'$_2$R'$_3$SiCH$_2$CH$_2$ groups and R'$_1$, R'$_2$, R'$_3$, which may be identical or different, represent a group selected from linear or branched alkyls comprising from 1 to 12 carbon atoms and the C6-C12 aryls,
- R$_2$ is selected from linear or branched alkyl groups comprising from 1 to 12 carbon atoms and pyrrolidine,
- J is selected from a single bond, a —CH$_2$—, —CH$_2$CH$_2$—, —CH$_2$OCH$_2$— and —CH$_2$OPhOCH$_2$— group, where Ph is a benzyl,
- ☐ represents a solid support,
- D is a protective group of alcohols,
- W is selected from C1-C12 alkane triyl groups, C6-C18 aryl triyl groups and C6-C18 aralkane triyl groups,
- Z is selected from C1-C12 alkoxy groups, oxygen-containing or nitrogen-containing C3-C12 cycloheteroalkyl groups, C1-C12 NCO-alkyl groups, C1-C12 CON-alkyl groups,
- Y is selected from linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups,
- X is selected from linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups, R is selected from C1-C12 acyl, C1-C12 S-alkyl, C6-C12 S-aryl, S-2-pyridine, oxygen-containing or nitrogen-containing C1-C12 S-heteroalkyl, C3-C12 S-cycloalkyl, oxygen-containing or nitrogen-containing C3-C12 S-cycloheteroalkyl groups.

2. The compound according to claim 1, corresponding to one of the formulas (Ia), (Ib) and (Ic) below:

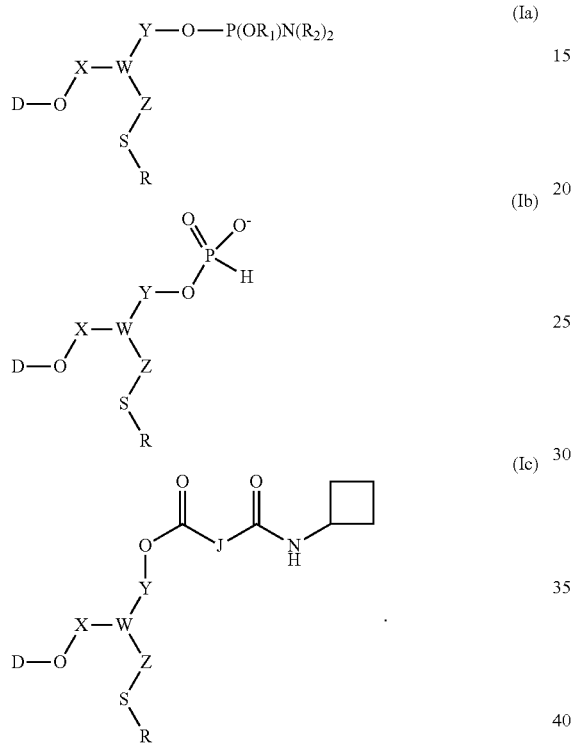

3. The compound according to claim 1, wherein:
D is selected from 4,4'-dimethoxytrityl, 9-phenylxanthen-9-yl or fluorenylmethoxycarbonyl;
W is selected from C1-C6 alkane triyl groups, a C6-C12 aryl triyl group, a C6-C12 aralkane triyl group, more particularly from CH, CCH$_3$, CCH$_2$CH$_3$, cyclohexane triyl and benzene triyl groups; and/or
Z is selected from C1-C6 alkoxy groups, oxygen-containing or nitrogen-containing C3-C6 cycloheteroalkyl groups, C1-C6 NCO-alkyl groups, C1-C6 CON-alkyl groups; and/or
Y is selected from linear or branched C1-C6 alkyl groups, C1-C6 aminoalkyl groups, C1-C6 alkoxy groups, C3-C6 cycloalkyl groups, oxygen-containing or nitrogen-containing C3-C6 cycloheteroalkyl groups; and/or
X is selected from linear or branched C1-C6 alkyl groups, C1-C6 aminoalkyl groups, C1-C6 alkoxy groups, C3-C6 cycloalkyl groups, oxygen-containing or nitrogen-containing C3-C6 cycloheteroalkyl groups; and/or
R is selected from C1-C6 acyl, C1-C6 S-alkyl, C6-C6 S-aryl, oxygen-containing or nitrogen-containing C1-C6 S-heteroalkyl, C3-C6 S-cycloalkyl, oxygen-containing or nitrogen-containing C3-C6 S-cycloheteroalkyl groups, preferably R is a C1-C6 acyl group.

4. The compound according to claim 1, wherein T is a group —O—P(OR$_1$)N(R$_2$)$_2$ where R$_2$ is an isopropyl group and R$_1$ is chosen from 2-cyanoethyl, 2-(trimethylsilyl)ethyl, 2-(triphenylsilyl)ethyl, 2-(diphenylmethylsilyl)ethyl groups.

5. The compound according to claim 1, wherein T is a group —OC(O)JC(O)NH-□ where □ is a solid support selected from resins, in particular from resins based on polystyrene, polyacrylamide, polyethyleneglycol, cellulose, polyethylene, polyester, latex, polyamide, polydimethylacrylamide, hydrophilic natural or synthetic polymers, glass beads, silica gels.

6. An oligomer having the formula:

in which:
(Ic) has the following formula,

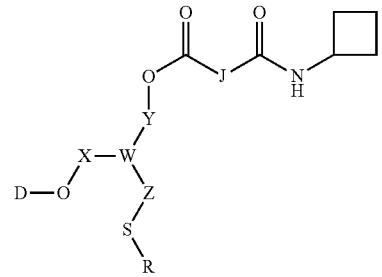

k represents an integer between 1 and 12,
(Δ) represents (I'a) or (I'b), with:

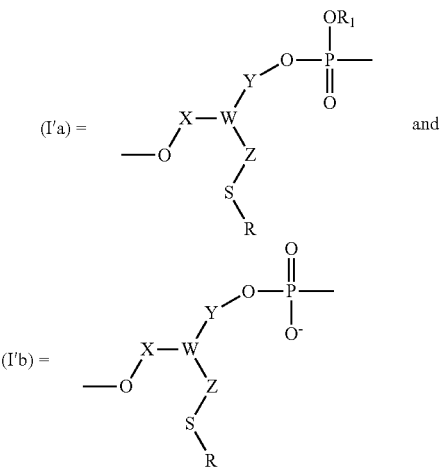

the formulae (Ic), (I'a) and (I'b) in which
□ represents a solid support,
D is a protective group of alcohols,
W is selected from C1-C12 alkane triyl groups, C6-C18 aryl triyl groups and C6-C18 aralkane triyl groups,
Z is selected from C1-C12 alkoxy groups, oxygen-containing or nitrogen-containing C3-C12 cycloheteroalkyl groups, C1-C12 NCO-alkyl groups, C1-C12 CON-alkyl groups,
Y is selected from linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups, X is selected from linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups, J is selected from a single bond, a —CH$_2$—, —CH$_2$CH$_2$—, —CH$_2$OCH$_2$— and —CH$_2$OPhOCH$_2$— group, where Ph is a benzyl, R is selected from C1-C12 acyl, C1-C12 S-alkyl, C6-C12 S-aryl, S-2-pyridine, oxygen-containing or nitrogen-containing C1-C12 S-heteroalkyl, C3-C12 S-cycloalkyl, oxygen-containing or nitrogen-containing C3-C12 S-cycloheteroalkyl groups being understood that R can further represent H, and R$_1$ is selected from 2-cyanoethyl and R'$_1$R'$_2$R'$_3$SiCH$_2$CH$_2$ groups, and R'$_1$, R'$_2$, R'$_3$, which may be identical or different, represent a group selected from linear or branched alkyls comprising from 1 to 12 carbon atoms and C6-C12 aryls.

7. The oligomer according to claim 6, having the formula (XIV)$_k$:

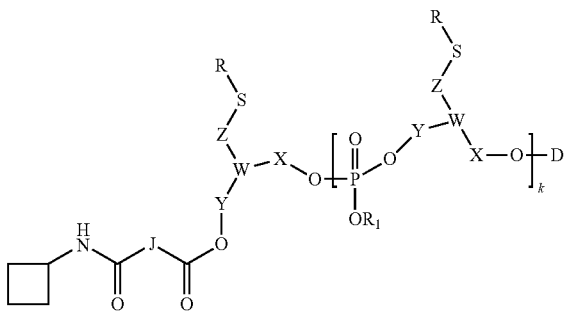

(XIV)$_k$ in which:
□, D, J, X, Y, W, Z, R and R$_1$ have the same definition as in claim 6, and D can further represent H,
k is an integer comprised between 1 and 11.

* * * * *